(12) United States Patent
Oda et al.

(10) Patent No.: US 9,238,665 B2
(45) Date of Patent: Jan. 19, 2016

(54) METHOD FOR PRODUCING AROMATIC COMPOUND

(71) Applicant: Sumitomo Chemical Company, Limited, Tokyo (JP)

(72) Inventors: Seiji Oda, Osaka (JP); Takashi Kamikawa, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/410,473

(22) PCT Filed: Jul. 5, 2013

(86) PCT No.: PCT/JP2013/069074
§ 371 (c)(1),
(2) Date: Dec. 22, 2014

(87) PCT Pub. No.: WO2014/007404
PCT Pub. Date: Jan. 9, 2014

(65) Prior Publication Data
US 2015/0322101 A1  Nov. 12, 2015

(30) Foreign Application Priority Data
Jul. 6, 2012  (JP) .................. 2012-152170

(51) Int. Cl.
*C07F 9/50* (2006.01)
*C07F 9/54* (2006.01)
*C08G 61/10* (2006.01)
*C08G 61/12* (2006.01)
*C07C 209/68* (2006.01)

(52) U.S. Cl.
CPC ............. *C07F 9/5022* (2013.01); *C07C 209/68* (2013.01); *C07F 9/5442* (2013.01)

(58) Field of Classification Search
CPC .... C07F 9/5022; C07F 9/5442; C07C 209/68
USPC .......... 528/8; 556/22; 564/307; 568/9, 13, 17
See application file for complete search history.

(56) References Cited

U.S. PATENT DOCUMENTS

| | | | |
|---|---|---|---|
| 5,514,805 A * | 5/1996 | Broger ................. | C07D 401/06 546/176 |
| 2009/0048413 A1* | 2/2009 | Oda ....................... | C08G 61/02 528/7 |
| 2010/0041898 A1* | 2/2010 | Busacca ................. | B01J 31/189 548/334.1 |
| 2010/0144999 A1* | 6/2010 | Yokozawa ............. | C08G 61/02 528/8 |
| 2010/0176376 A1 | 7/2010 | Suzuki et al. | |
| 2012/0116036 A1* | 5/2012 | Nozaki ................. | C08F 210/02 526/171 |

FOREIGN PATENT DOCUMENTS

| | | |
|---|---|---|
| JP | 2008045110 A | 2/2008 |
| WO | 2007101820 A1 | 9/2007 |
| WO | WO 2012133874 A1 * | 10/2012 |

OTHER PUBLICATIONS

International Search Report issued Aug. 6, 2013 in International Application No. PCT/JP2013/069074.
Lü et al., "Application of Dicyclohexyl-(S)-trimethoxyphenyl Phosphine-HBF4 Salt for the Highly Selective Suzuki Coupling of the C—Cl Bond in b-Chlorobutenolides Over the More Reactive Allylic C—O Bond," Chemistry—A European Journal, vol. 16, pp. 6434-6437 (2010).
Grabulosa et al., "Palladium complexes of bulky ortho-trifluoromethylphenyl-substituted phosphines: Unusually regioselective catalysts for the hydroxycarbonylation and alkoxycarbonylation of alkenes," Journal of Molecular Catalysis A: Chemical, vol. 330, pp. 18-25 (2010).

* cited by examiner

*Primary Examiner* — Porfirio Nazario Gonzalez
(74) *Attorney, Agent, or Firm* — Panitch Schwarze Belisario & Nadel LLP

(57) ABSTRACT

A method is provided for producing an aromatic compound, including a step of mixing a compound represented by formula (A) and a compound represented by formula (B):

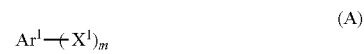

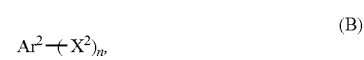

in the presence of at least one phosphine compound selected from the group consisting of a phosphine represented by formula (C) and a phosphonium salt represented by formula (F):

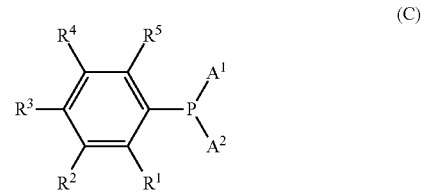

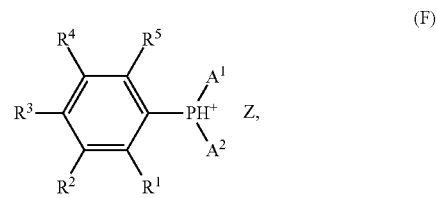

a base, a palladium compound, and an aprotic organic solvent.

19 Claims, No Drawings

METHOD FOR PRODUCING AROMATIC COMPOUND

CROSS-REFERENCE TO RELATED APPLICATION

This application is a Section 371 of International Application No. PCT/JP2013/069074, filed Jul. 5, 2013, which was published in the Japanese language on Jan. 9, 2014, under International Publication No. WO 2014/007404 A1, and the disclosure of which is incorporated herein by reference.

TECHNICAL FIELD

The present invention relates to a production method of an aromatic compound.

BACKGROUND ART

An aromatic compound having a structure in which two or more aromatic rings are n-conjugated is useful, for example, for an organic electronics material. As a method for producing the aromatic compound, a method of production by subjecting an aromatic monomer to the Suzuki coupling reaction is known.

Specifically, Patent document 1 describes a method of polymerizing bis(4-bromophenyl) [4-(2-butyl)phenyl]amine and a boronate formed of 9,9-di-n-octylfluorene-2,7-diboronic acid and pinacol (tetramethyl ethylene glycol) in the presence of palladium acetate, tris(2-methoxyphenyl)phosphine, a tetraethylammonium hydroxide aqueous solution and toluene, to produce the corresponding aromatic compound.

PRIOR ART DOCUMENT

Patent Document

[Patent document 1] JP-A No. 2007-126652

SUMMARY OF THE INVENTION

Problem to be Solved by the Invention

The present invention has an object of providing a novel method of producing an aromatic compound.

Means for Solving the Problem

Under such conditions, the present inventors have intensively studied a method for producing an aromatic compound, resultantly leading to the present invention.

That is, the present invention provides,

[1] A method of producing an aromatic compound, comprising a step of mixing a compound represented by the formula (A):

(wherein, $X^1$ represents a group represented by the formula (1), (2), (3), (4), (5) or (6):

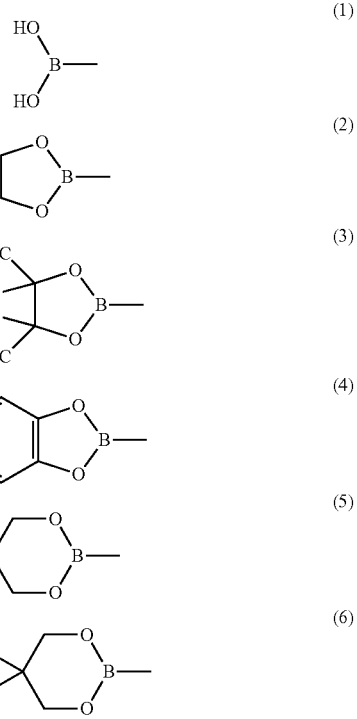

$Ar^1$ represents a monovalent or divalent aromatic hydrocarbon group having a number of carbon atoms of 6 to 36, and m represents 1 or 2. A carbon atom contained in the aromatic hydrocarbon group may be substituted with a hetero atom or a carbonyl group, and a hydrogen atom contained in the aromatic hydrocarbon group may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group.)

and a compound represented by the formula (B):

(wherein, $X^2$ represents a chlorine atom, a bromine atom, an iodine atom, an alkylsulfonyloxy group, a fluorine-substituted alkylsulfonyloxy group or an arylsulfonyloxy group, $Ar^2$ represents a monovalent or divalent aromatic hydrocarbon group having a number of carbon atoms of 6 to 36, and n represents 1 or 2. A carbon atom contained in the aromatic hydrocarbon group may be substituted with a hetero atom or a carbonyl group, and a hydrogen atom contained in the aromatic hydrocarbon group may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group.) in the presence of at least one phosphine compound selected from the group consisting of a phosphine represented by the formula (C):

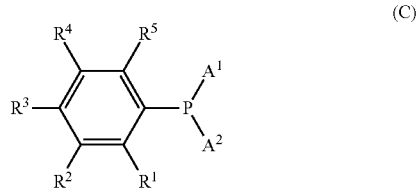

(wherein, $A^1$ and $A^2$ represent each independently a cyclopentyl group which may have a substituent. $R^1$ and $R^5$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20, an aryloxy group having a number of carbon atoms of 6 to 20, a group represented by the formula (D):

(wherein, $R^6$ represents a hydrogen atom, an alkyl group having a number of carbon atoms of 1 to 20 or a cycloalkyl group having a number of carbon atoms of 3 to 20, $R^7$ and $R^8$ represent each independently an alkyl group having a number of carbon atoms of 1 to 20 or a cycloalkyl group having a number of carbon atoms of 3 to 20, and $R^7$ and $R^8$ may be linked to form a ring.)
or a group represented by the formula (E):

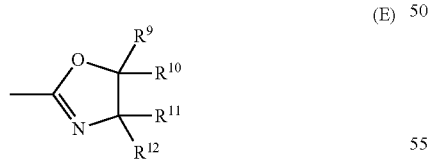

(wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20.),
$R^2$, $R^3$ and $R^4$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20. Here, all of $R^1$ to $R^5$ do not simultaneously represent a hydrogen atom, and, when at least one of $R^1$ to $R^5$ is a fluoroalkyl group having a number of carbon atoms of 1 to 20, at least one of the remaining $R^1$ to $R^5$ is not a hydrogen atom or a fluoroalkyl group having a number of carbon atoms of 1 to 20. Further, $R^2$ and $R^3$ may be linked to form a ring together with a carbon atom to which they are linked, and $R^3$ and $R^4$ may be linked to form a ring together with a carbon atom to which they are linked.)
and a phosphonium salt represented by the formula (F):

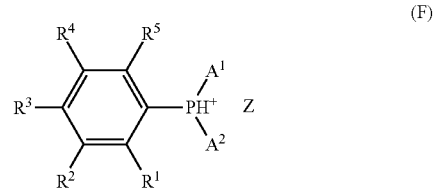

(wherein, $A^1$, $A^2$, $R^1$ to $R^5$ represent the same meaning as described above, and Z represents an anion.),
a base, a palladium compound and an aprotic organic solvent,

[2] The production method of an aromatic compound according to [1], wherein $A^1$ and $A^2$ are a cyclopentyl group which may have an alkyl group having a number of carbon atoms of 1 to 20 or an aryl group having a number of carbon atoms of 6 to 20 as a substituent,

[3] The production method of an aromatic compound according to [1] or [2], wherein $A^1$ and $A^2$ are a cyclopentyl group,

[4] The production method of an aromatic compound according to any one of [1] to [3] wherein at least one selected from $R^1$ and $R^5$ is an alkoxy group having a number of carbon atoms of 1 to 20,

[5] The production method of an aromatic compound according to any one of [1] to [4] wherein $R^2$, $R^3$ and $R^4$ are a hydrogen atom,

[6] The production method of an aromatic compound according to [1], wherein the phosphine compound is at least one selected from the group consisting of a phosphine represented by the formula (G):

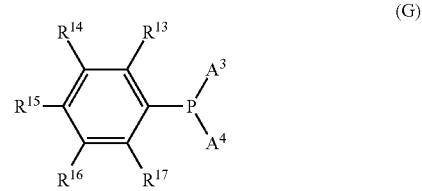

(wherein, $A^3$ and $A^4$ represent each independently a cyclopentyl group which may have a substituent. $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the formula (E):

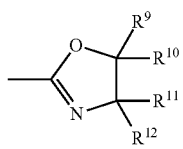

(E)

(wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20.), $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20. Here, all of $R^{13}$ to $R^{17}$ do not simultaneously represent a hydrogen atom, and, when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20. Further, $R^{14}$ and $R^{15}$ may be linked to form a ring together with a carbon atom to which they are linked, and $R^{15}$ and $R^{16}$ may be linked to form a ring together with a carbon atom to which they are linked.)

and a phosphonium salt represented by the formula (H):

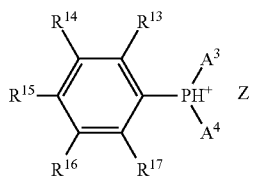

(H)

(wherein, $A^3$, $A^4$, $R^{13}$ to $R^{17}$ and Z represent the same meaning as described above.),

[7] The production method of an aromatic compound according to any one of [1] to [6], wherein the aprotic organic solvent is at least one selected from the group consisting of ether solvents, aromatic hydrocarbon solvents and aliphatic hydrocarbon solvents,

[8] The production method of an aromatic compound according to any one of [1] to [7], wherein the palladium compound is a palladium(0) complex or a palladium(II) complex,

[9] A phosphine represented by the formula (G):

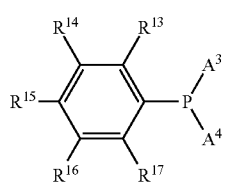

(G)

(wherein, $A^3$ and $A^4$ represent each independently a cyclopentyl group which may have a substituent. $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the formula (E):

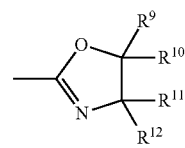

(E)

(wherein, $R^9$, $R_{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20.), $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20. Here, all of $R^{13}$ to $R^{17}$ do not simultaneously represent a hydrogen atom, and, when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20. Further, $R^{14}$ and $R^{15}$ may be linked to form a ring together with a carbon atom to which they are linked, and $R^{15}$ and $R^{16}$ may be linked to form a ring together with a carbon atom to which they are linked.),

[10] The phosphine according to [9], wherein $A^3$ and $A^4$ are a cyclopentyl group which may have an alkyl group having a number of carbon atoms of 1 to 20 or an aryl group having a number of carbon atoms of 6 to 20 as a substituent,

[11] The phosphine according to [9] or [10], wherein $A^3$ and $A^4$ are a cyclopentyl group,

[12] The phosphine according to any one of [9] to [11], wherein at least one selected from $R^{13}$ and $R^{17}$ is an alkoxy group having a number of carbon atoms of 1 to 20,

[13] The phosphine according to any one of [9] to [12], wherein $R^{17}$, $R^{15}$ and $R^{16}$ are a hydrogen atom,

[14] A phosphonium salt represented by the formula (H):

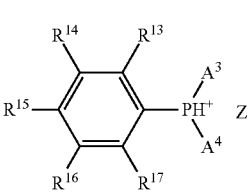

(H)

(wherein, $A^3$ and $A^4$ represent each independently a cyclopentyl group which may have a substituent. $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the formula (E):

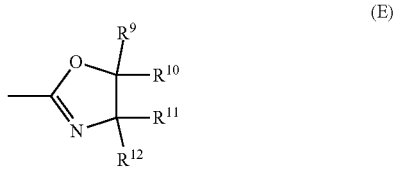

(wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20.), $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20. Here, all of $R^{13}$ to $R^{17}$ do not simultaneously represent a hydrogen atom, and, when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20. Further, $R^{14}$ and $R^{15}$ may be linked to form a ring together with a carbon atom to which they are linked, and $R^{15}$ and $R^{16}$ may be linked to form a ring together with a carbon atom to which they are linked. Z represents an anion.),

[15] The phosphonium salt according to [14], wherein $A^3$ and $A^4$ are a cyclopentyl group which may have an alkyl group having a number of carbon atoms of 1 to 20 or an aryl group having a number of carbon atoms of 6 to 20 as a substituent,

[16] The phosphonium salt according to [14] or [15], wherein $A^3$ and $A^4$ are a cyclopentyl group,

[17] The phosphonium salt according to any one of [14] to [16], wherein at least one selected from $R^{13}$ and $R^{17}$ is an alkoxy group having a number of carbon atoms of 1 to 20,

[18] The phosphonium salt according to any one of [14] to [17], wherein $R^{14}$, $R^{15}$ and $R^{16}$ are a hydrogen atom,

[19] A transition metal complex obtained by contacting the phosphine according to any one of [9] to [13] and a group X transition metal compound,

[20] A transition metal complex obtained by contacting the phosphonium salt according to any one of [14] to [18] and a group X transition metal compound, and the like.

Effect of the Invention

According to the production method of the present invention, an aromatic compound can be produced.

MODES FOR CARRYING OUT THE INVENTION

Compound Represented by the Formula (A) and
Compound Represented by the Formula (B)

The compound represented by the formula (A) used in the production method of the present invention includes a compound represented by the formula (A-1):

(hereinafter, referred to as a compound (A-1) in some cases) and a compound represented by the formula (A-2):

(hereinafter, referred to as a compound (A-2) in some cases), and the compound represented by the formula (B) includes a compound represented by the formula (B-1):

(hereinafter, referred to as a compound (B-1) in some cases) and a compound represented by the formula (B-2):

(hereinafter, referred to as a compound (B-2) in some cases).

$Ar^1$ and $Ar^2$ represent each independently a monovalent or divalent aromatic hydrocarbon group having a number of carbon atoms of 6 to 36. The monovalent or divalent aromatic hydrocarbon group includes a monovalent or divalent monocyclic aromatic hydrocarbon group, a monovalent or divalent condensed aromatic hydrocarbon group, and a monovalent or divalent group formed by linking two or more monocyclic aromatic hydrocarbon groups via a single bond, a hetero atom (an oxygen atom, a nitrogen atom, a sulfur atom or the like) or a carbonyl group (—CO—). Specific examples thereof include monovalent monocyclic aromatic hydrocarbon groups such as a phenyl group and the like, divalent monocyclic aromatic hydrocarbon groups such as a phenylene group and the like, monovalent condensed aromatic hydrocarbon groups such as a naphthyl group, an anthracenyl group, a fluorenyl group and the like, divalent condensed aromatic hydrocarbon groups such as a naphthalenediyl group, an anthracenediyl group, a fluorenediyl group and the like, monovalent groups formed by linking two or more monocyclic aromatic hydrocarbon groups via a single bond, a hetero atom (an oxygen atom, a nitrogen atom, a sulfur atom or the like) or carbonyl group such as a biphenyl group and the like, and divalent groups formed by linking two or more monocyclic aromatic hydrocarbon groups via a single bond, a hetero atom (an oxygen atom, a nitrogen atom, a sulfur atom or the like) or a carbonyl group such as a biphenylene group and the like. A carbon atom contained in the aromatic hydrocarbon group may be substituted with a hetero atom such as an oxygen atom, a nitrogen atom, a sulfur atom and the like or a carbonyl group.

A hydrogen atom contained in the above-described monovalent or divalent aromatic hydrocarbon group having a number of carbon atoms of 6 to 36 may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group. A hydrogen atom contained in these substituents may be substituted with a fluorine atom, an alkoxy group having a number of carbon atoms of 1 to 20, an aryl group having a number of carbon atoms of 6 to 20, an aryloxy group having a number of carbon atoms of 6 to 20, an acyl group having a number of carbon atoms of 2 to 20 or a cyano group.

"Alkyl group" includes an alkyl group having a number of carbon atoms of 1 to 20, and may be linear or branched. Specific examples thereof include a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group.

"Cycloalkyl group" includes a cycloalkyl group having a number of carbon atoms of 3 to 20, and specifically includes a cyclopropyl group, a cyclopentyl group, a cyclohexyl group, a cycloheptyl group and a cyclooctyl group.

"Alkoxy group" includes an alkoxy group having a number of carbon atoms of 1 to 20, and may be linear or branched. Specific examples thereof include a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-icosyloxy group.

"Cycloalkoxy group" includes a cycloalkoxy group having a number of carbon atoms of 3 to 20, and specifically includes a cyclopropoxy group, a cyclopentyloxy group, a cyclohexyloxy group, a cycloheptyloxy group and a cyclooctyloxy group.

"Alkylthio group" includes an alkylthio group having a number of carbon atoms of 1 to 20, and may be linear or branched. Specific examples thereof include a methylthio group, an ethylthio group, a n-propylthio group, an isopropylthio group, a n-butylthio group, an isobutylthio group, a sec-butylthio group, a tert-butylthio group, a n-pentylthio group, a n-hexylthio group, a n-heptylthio group, a n-octylthio group, a 2-ethylhexylthio group, a n-nonylthio group, a n-decylthio group, a 3,7-dimethyloctylthio group and a n-dodecylthio group.

"Cycloalkylthio group" includes a cycloalkylthio group having a number of carbon atoms of 3 to 20, and specifically includes a cyclopropylthio group, a cyclopentylthio group, a cyclohexylthio group, a cycloheptylthio group and a cyclooctylthio group.

"Aryl group" includes an aryl group having a number of carbon atoms of 6 to 20. Specific examples thereof include a phenyl group, a 4-methylphenyl group, a 2-methylphenyl group, a 1-naphthyl group, a 2-naphthyl group, a 3-phenanthryl group and a 2-anthryl group and the like.

"Aryloxy group" includes a group formed by linking an oxygen atom to the above-described aryl group having a number of carbon atoms of 6 to 20. Specific examples thereof include a phenoxy group, a naphthyloxy group, a phenanthryloxy group and an anthryloxy group and the like.

"Arylthio group" includes a group formed by linking a sulfur atom to the above-described aryl group having a number of carbon atoms of 6 to 20. Specific examples thereof include a phenylthio group and a naphthylthio group.

"Arylalkyl group" includes a group obtained by substituting a hydrogen atom of the above-described alkyl group having a number of carbon atoms of 1 to 20 with the above-described aryl group having a number of carbon atoms of 6 to 20, and specifically includes a phenylmethyl group, a naphthylmethyl group and the like.

"Arylcycloalkyl group" includes a phenylcyclohexyl group, a naphthylcyclohexyl group, a phenylcyclopentyl group and the like.

"Arylalkenyl group" includes a phenylalkenyl group and a naphthylalkenyl group. "Alkenyl group" includes an alkenyl group having a number of carbon atoms of 2 to 8 such as a vinyl group, a 1-propenyl group, a 2-propenyl group, a 1-butenyl group, a 2-butenyl group, a 1-pentenyl group, a 2-pentenyl group, a 1-hexenyl group, a 2-hexenyl group, a 1-octenyl group and the like.

"Arylalkynyl group" includes a phenylalkynyl group and a naphthylalkynyl group. "Alkynyl group" includes an alkynyl group having a number of carbon atoms of 2 to 8 such as an ethynyl group, a 1-propynyl group, a 2-propynyl group, a 1-butynyl group, a 2-butynyl group, a 1-pentynyl group, a 2-pentynyl group, a 1-hexynyl group, a 2-hexynyl group, a 1-octynyl group and the like.

"Heterocyclic group which may have a substituent" denotes a group obtained by converting one hydrogen atom in a heterocyclic compound which may have a substituent into a connecting bond. The heterocyclic group includes a thienyl group, an alkylthienyl group, a pyrrolyl group, a furyl group, a pyridyl group, an alkylpyridyl group, a pyridazinyl group, a pyrimidyl group, a pyrazinyl group, a triazinyl group, a pyrrolidinyl group, a piperidinyl group, a quinolyl group and an isoquinolyl group. The substituent carried on the above-described heterocyclic group includes an alkyl group, and specifically, the above-described alkyl group having a number of carbon atoms of 1 to 20.

"Amino group which may have a substituent" denotes a group represented by —N(R')$_2$, and two R' represent each independently a hydrogen atom or a substituent. The substituent includes a hydrocarbon group having a number of carbon atoms of 1 to 20 such as an alkyl group, a cycloalkyl group, an aryl group and the like, and a heterocyclic group which may have a substituent. Preferably, it is an amino group having a substituent, namely, an amino group in which at least one R' is a substituent. Specific examples of "amino group which may have a substituent" include a methylamino group, a dimethylamino group, an ethylamino group, a diethylamino group, a n-propylamino group, a di-n-propylamino group, an isopropylamino group, a diisopropylamino group, a n-butylamino group, an isobutylamino group, a sec-butylamino group, a tert-butylamino group, a n-pentylamino group, a n-hexylamino group, a n-heptylamino group, a n-octylamino group, a 2-ethylhexylamino group, a n-nonylamino group, a n-decylamino group, a 3,7-dimethyloctylamino group, a n-dodecylamino group, a cyclopentylamino group, a dicyclopentylamino group, a cyclohexylamino group, a dicyclohexylamino group, a bis(trifluoromethyl)amino group, a phenylamino group, a diphenylamino group, a naphthylamino group, a pyridylamino group, a pyridazinylamino group, a pyrimidinylamino group, a pyrazinylamino group and a triazinylamino group.

"Silyl group which may have a substituent" denotes a group represented by —Si(R')$_3$, and three R' represent each independently a hydrogen atom or a substituent. R' includes a hydrocarbon group having a number of carbon atoms of 1 to 20 such as an alkyl group, a cycloalkyl group, an aryl group and the like, and a heterocyclic group which may have a substituent. Preferably, it is a silyl group which has a substituent, namely, a silyl group in which at least one R' is a substituent. Specific examples of "silyl group which may have a substituent" include a trimethylsilyl group, a triethylsilyl group, a tri-n-propylsilyl group, a triisopropylsilyl group, a dimethylisopropylsilyl group, a diethylisopropylsilyl group, a tert-butylsilyldimethylsilyl group, a n-pentyldimethylsilyl group, a n-hexyldimethylsilyl group, a n-heptyldimethylsilyl group, a n-octyldimethylsilyl group, a 2-ethylhexyldimethylsilyl group, a n-nonyldimethylsilyl group, a n-decyldimethylsilyl group, a 3,7-dimethyloctyldimethylsilyl group, a n-dodecyldimethylsilyl group, a phenylalkylsilyl group, an alkoxyphenylalkylsilyl group, an alkylphenylalkylsilyl group, a naphthylalkylsilyl group, a phenylallyldimethylsilyl group, a triphenylsilyl group, a tri-p-xylylsilyl group, a tribenzylsilyl group, a diphenylmethylsilyl group, a tert-butyldiphenylsilyl group and a dimethylphenylsilyl group.

"Acyl group" includes an aliphatic acyl group such as an acetyl group, a propionyl group, a butylyl group, an isobutylyl group and the like and an aromatic acyl group such as a benzoyl group, a naphthoyl group and the like.

"Group having a carbon atom-nitrogen atom double bond as a partial structure" denotes a group formed by removing from an imine compound having a partial structure represented by at least one of the formula: H—N=C< and the formula: —N=CH— a hydrogen atom in the partial structure (hereinafter, referred to as imine residue in some cases), and includes those in which a ring is not formed based on the above-described "carbon atom-nitrogen atom double bond". "Imine compound" includes an aldimine, a ketimine and a compound obtained by substituting a hydrogen atom linked to a nitrogen atom in an aldimine with a substituent such as an alkyl group, an aryl group, an arylalkyl group, an arylalkenyl group, an arylalkynyl group and the like. The imine residue has a number of carbon atoms of usually 2 to 20, preferably 2 to 18, more preferably 2 to 16.

"Imine residue" includes a group represented by the formula: —CR"=N—R'" and a group represented by the formula: —N=C(R'")$_2$ (wherein, R" represents a hydrogen atom, an alkyl group, an aryl group, an arylalkyl group, an arylalkenyl group or an arylalkynyl group, and a plurality of R'" represent each independently an alkyl group, a cycloalkyl group, an aryl group, an arylalkyl group, an arylcycloalkyl group, an arylalkenyl group or an arylalkynyl group. Here, when two R'" exist, two R'" are mutually linked to form a divalent group, specifically, an alkylene group having a number of carbon atoms of 2 to 18 such as an ethylene group, a trimethylene group, a tetramethylene group, a pentamethylene group, a hexamethylene group and the like.).

Specific examples of "imine residue" include groups shown below.

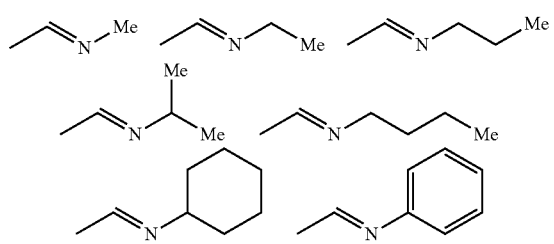

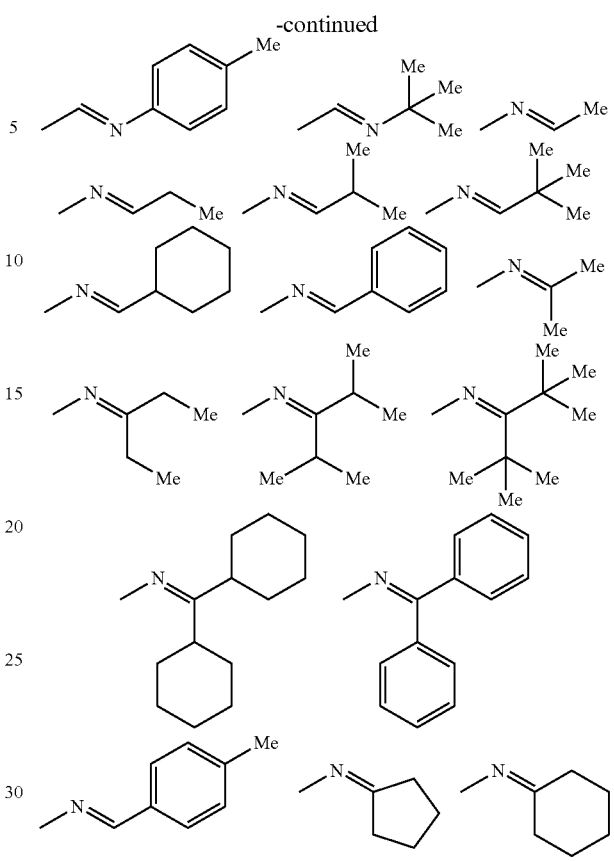

"Acid imide group" denotes a residue obtained by converting a hydrogen atom linking to a nitrogen atom contained in an acid imide into a connecting bond. The acid imide group has a number of carbon atoms of preferably 4 to 20, more preferably 4 to 18, further preferably 4 to 16. Specific examples of "acid imide group" include groups shown below.

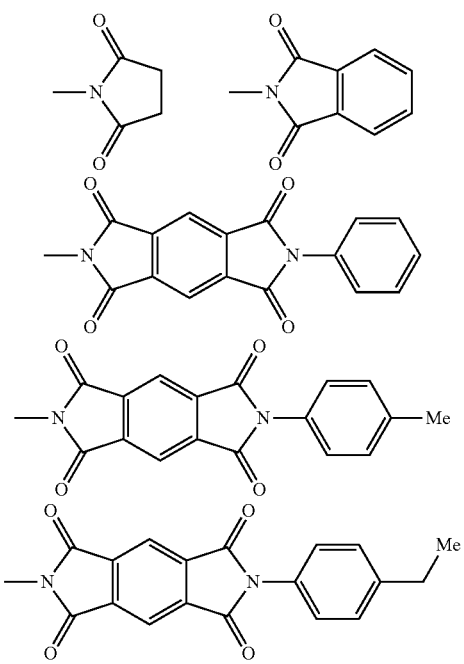

"Alkoxycarbonyl group" includes a group formed by linking a carbonyl group to the above-described alkoxy group. Specific examples thereof include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, a n-hexyloxycarbonyl group, a n-heptyloxycarbonyl group, a n-octyloxycarbonyl group, a 2-ethylhexyloxycarbonyl group, a n-nonyloxycarbonyl group, a n-decyloxycarbonyl group, a 3,7-dimethyloctyloxycarbonyl group, a n-dodecyloxycarbonyl group, a trifluoromethoxycarbonyl group, a pentafluoroethoxycarbonyl group, a perfluorobutoxycarbonyl group, a perfluorohexyloxycarbonyl group and a perfluorooctyloxycarbonyl group.

"Cycloalkoxycarbonyl group" includes a group formed by linking a carbonyl group to the above-described cycloalkoxy group. Specifically, a cyclohexyloxycarbonyl group is mentioned.

"Aryloxycarbonyl group" includes a group formed by linking a carbonyl group to the above-described aryloxy group. Specific examples thereof include a phenoxycarbonyl group, a naphthoxycarbonyl group and a pyridyloxycarbonyl group.

The aromatic hydrocarbon group includes monovalent or divalent groups represented by the formulae (a-1) to (e-1) and the formulae (a-2) to (e-2).

(wherein, R represents a substituent, and p represents an integer of 0 to 4.)

The above-described substituent includes the same groups as exemplified as the substituent of $Ar^1$ and $Ar^2$.

The aromatic hydrocarbon group obtained by substituting a carbon atom contained in an aromatic hydrocarbon group with a hetero atom or a carbonyl group includes monovalent or divalent groups represented by the formulae (f-1) to (z-1) and the formulae (f-2) to (z-2).

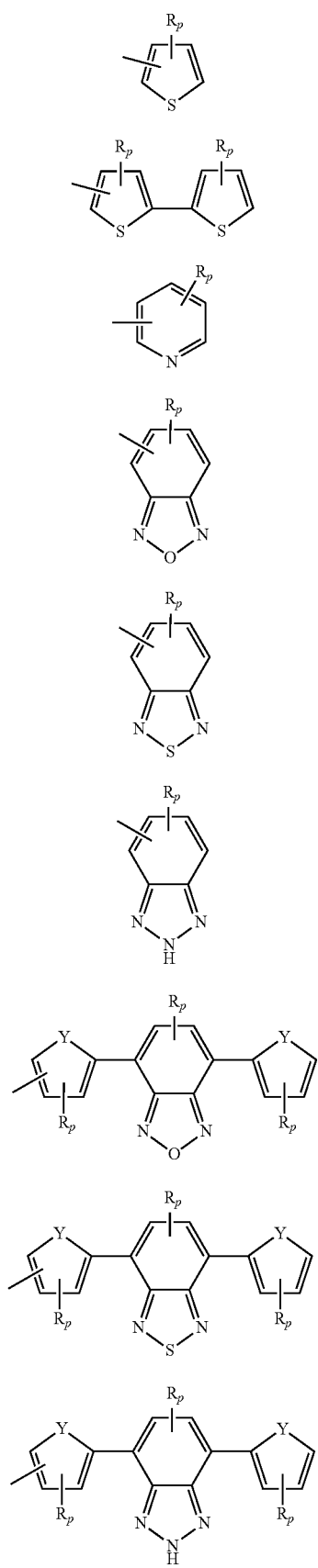
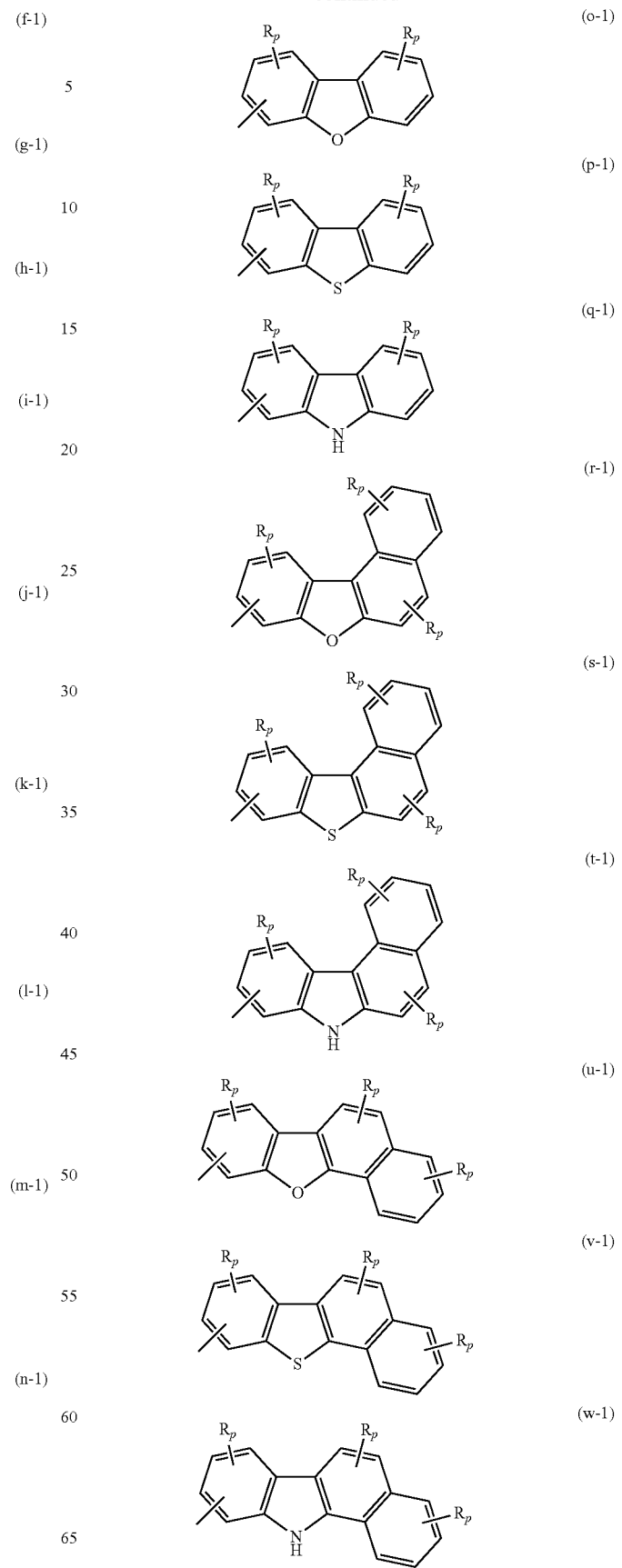

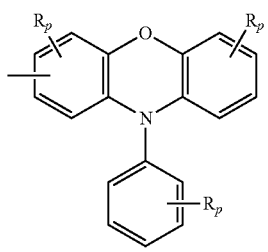
(x-1)
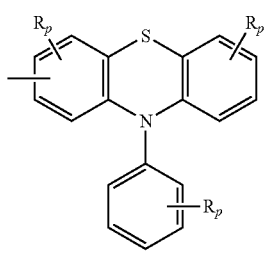
(y-1)
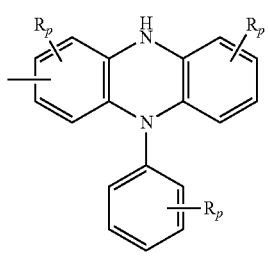
(z-1)
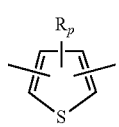
(f-2)
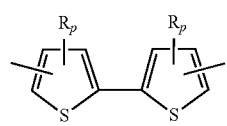
(g-2)
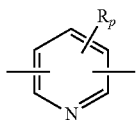
(h-2)
(i-2)
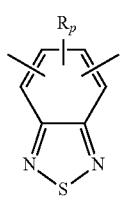
(j-2)
(k-2)
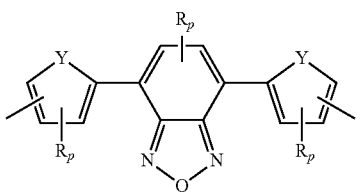
(l-2)
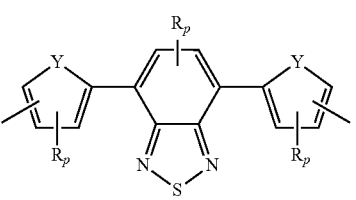
(m-2)
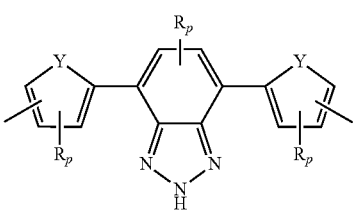
(n-2)
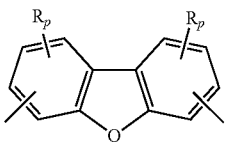
(o-2)
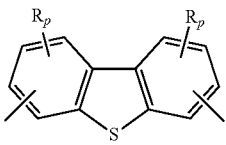
(p-2)
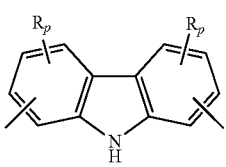
(q-2)
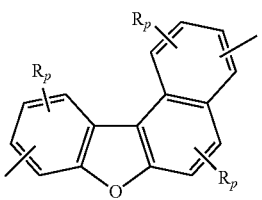
(r-2)

(s-2)
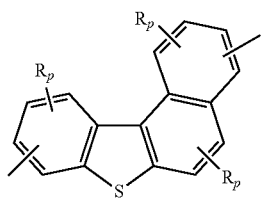

(t-2)
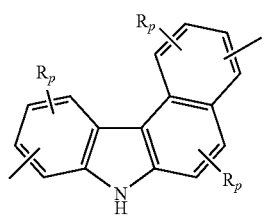

(u-2)
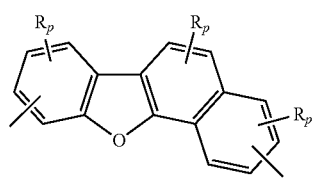

(v-2)
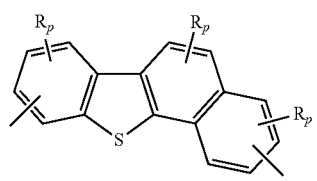

(w-2)
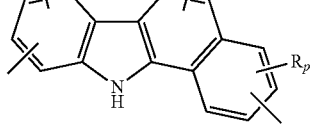

(x-2)
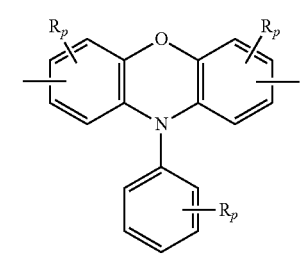

(y-2)
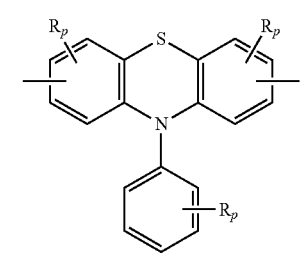

(z-2)
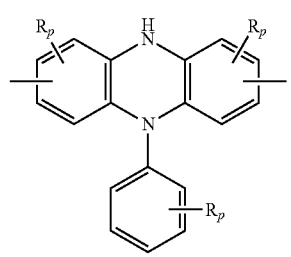

(wherein, R represents a substituent, p represents an integer of 0 to 4, and Y represents N, S or C=O.)

The above-described substituent includes the same groups as exemplified as the substituent of Ar¹ and Ar².

The monovalent or divalent group formed by linking two or more monocyclic aromatic hydrocarbon groups via a single bond, a hetero atom or a carbonyl group includes monovalent or divalent groups represented by the formulae (aa-1) to (ae-1) or the formulae (aa-2) to (ae-2).

(aa-1)
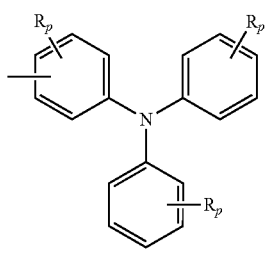

(ab-1)
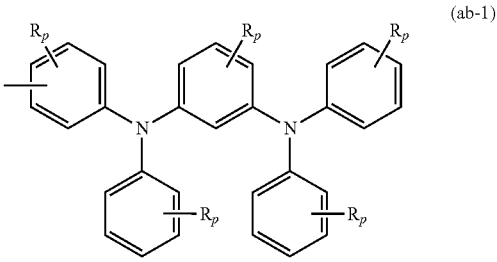

(ac-1)
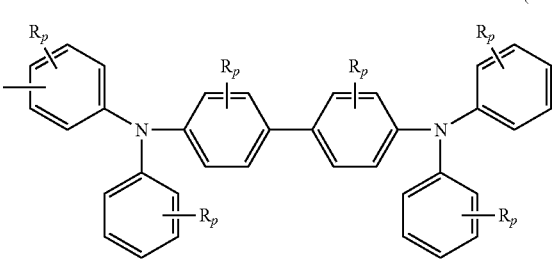

(ad-1)
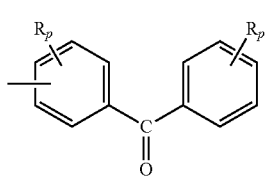

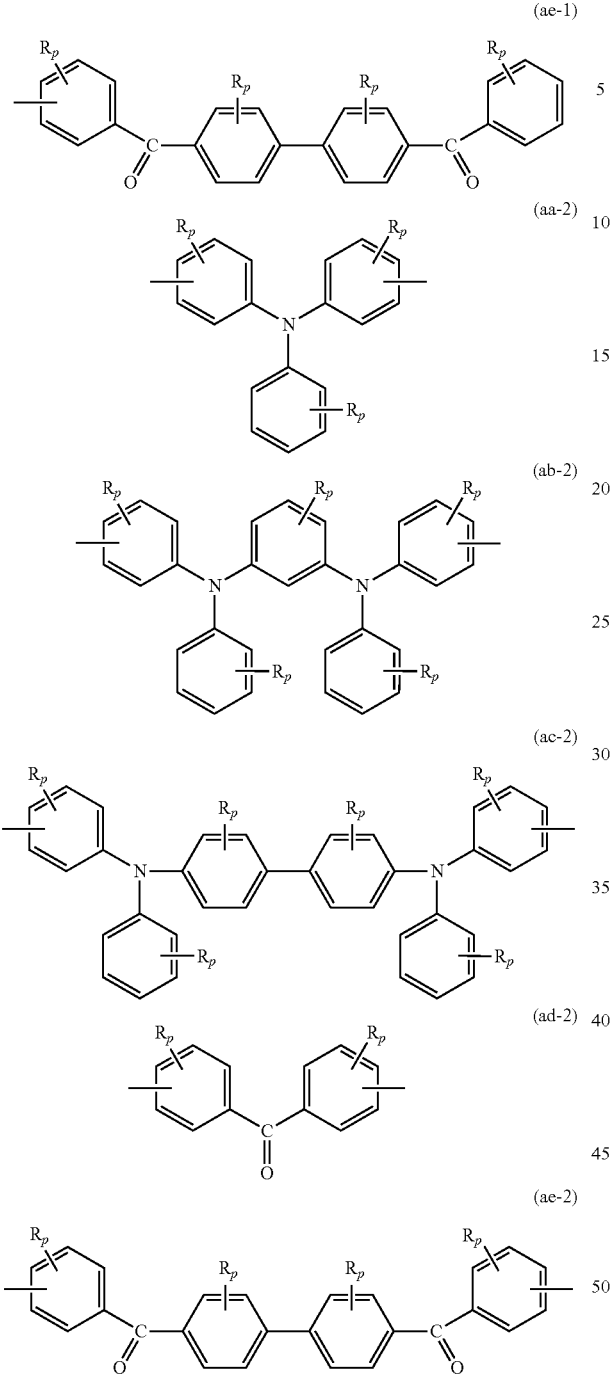

(1)

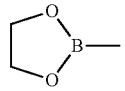

(2)

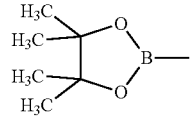

(3)

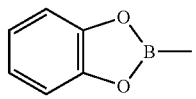

(4)

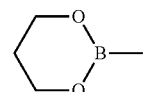

(5)

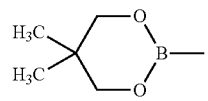

(6)

(wherein, R represents a substituent, and p represents an integer of 0 to 4.)

The above-described substituent includes the same groups as exemplified as the substituent of Ar¹ and Ar².

Ar¹ in the above-described formula (A) and Ar² in the above-described formula (B) may be the same or different.

Preferable examples of Ar¹ and Ar² include groups represented by the formula (a-1), (a-2), (b-1), (b-2), (c-1), (c-2), (d-1), (d-2), (e-1), (e-2), (m-1), (m-2) (Y in (m-1) and (m-2) is preferably S), (y-1), (y-2), (aa-1) or (aa-2).

X¹ in the above-described formula (A) represents a group represented by the formula (1), (2), (3), (4), (5) or (6).

Preferably, X¹ is a group represented by the formula (1), (2), (3) or (5).

The compound represented by the above-described formula (A-1) includes phenylboronic acid, o-tolylboronic acid, m-tolylboronic acid, p-tolylboronic acid, 2,3-dimethylphenylboronic acid, 2,4-dimethylphenylboronic acid, 2,5-dimethylphenylboronic acid, 2,6-dimethylphenylboronic acid, 2,4,6-trimethylphenylboronic acid, 2,3,5,6-tetramethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluoromethylphenylboronic acid, 3,5-bis(trifluoromethyl)phenylboronic acid, 2-methoxyphenylboronic acid, 3-methoxyphenylboronic acid, 4-methoxyphenylboronic acid, 2,4-dimethoxyphenylboronic acid, 2,5-dimethoxyphenylboronic acid, 2,6-dimethoxyphenylboronic acid, 3,4-dimethoxyphenylboronic acid, 2-ethoxyphenylboronic acid, 3-ethoxyphenylboronic acid, 4-ethoxyphenylboronic acid, 2-(benzyloxy)phenylboronic acid, 2-phenoxyphenylboronic acid, 4-phenoxyphenylboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 3,4-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 2-acetylphenylboronic acid, 3-acetylphenylboronic acid, 4-acetylphenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-diethylaminomethyl)phenylboronic acid, furan-2-boronic acid, furan-3-boronic acid, 5-formylfuran-2-boronic acid, 3-formylfuran-2-boronic acid, benzofuran-2-boronic acid, dibenzofuran-4-boronic acid, thiophene-2-boronic acid, thiophene-3-boronic acid, 4-methylthiophene-2-boronic acid, 5-methylthiophene-2-boronic acid, 5-chlorothiophene-2-boronic acid, 2-acetylthiophene-5-boronic acid, 3-formylthiophene-2-boronic acid, benzothiophene-2-boronic acid, dibenzothiophene-4-boronic acid, pyrazole-4-boronic acid, 3-methylpyrazole-4-boronic acid, 3,5-dimethylpyrazole-4-boronic acid, thiazole-2-boronic acid, pyridine-3-boronic acid, pyridine-4-boronic acid, pyrimidine-5-boronic acid, quinoline-8-boronic acid, isoquinoline-4-boronic acid, 1,4-benzenediboronic acid, 4,4'-biphenyldiboronic acid, vinylboronic acid, 3-methyl-2-buten-2-ylboronic acid and the like.

The compound represented by the above-described formula (A-2) includes 2,2'-(9,9-dihexyl-9H-fluorene-2,7-diyl)bis(1,3,2-dioxaborolane), 2,2'-(9,9-dihexyl-9H-fluorene-2,7-diyl)bis(1,3,2-dioxaborinane), 2,2'-(9,9-dihexyl-9H-fluorene-2,7-diyl)bis(4,4,5,5-tetramethyl-1,3,2-dioxaborolane), 2,2'-(9,9-dihexyl-9H-fluorene-2,7-diyl)bis(5,5-dimethyl-1,3,2-dioxaborinane), 2,2'-(9,9-dioctyl-9H-fluorene-2,7-diyl)bis(1,3,2-dioxaborolane), 2,2'-(9,9-dioctyl-9H-fluorene-2,7-diyl)bis(1,3,2-dioxaborinane), 2,2'-(9,9-dioctyl-9H-fluorene-2,7-diyl)bis(4,4,5,5-tetramethyl-1,3,2-dioxaborolane), 2,2'-(9,9-dioctyl-9H-fluorene-2,7-diyl)bis(5,5-dimethyl-1,3,2-dioxaborinane), 2,2'-(9,9-didodecyl-9H-fluorene-2,7-diyl)bis(1,3,2-dioxaborolane), 2,2'-(9,9-didodecyl-9H-fluorene-2,7-diyl)bis(1,3,2-dioxaborinane), 2,2'-(9,9-didodecyl-9H-fluorene-2,7-diyl)bis(4,4,5,5-tetramethyl-1,3,2-dioxaborolane), 2,2'-(9,9-didodecyl-9H-fluorene-2,7-diyl)bis(5,5-dimethyl-1,3,2-dioxaborinane), 2,2'-(3,5-dimethoxy-9,9-dihexyl-9H-fluorene-2,7-diyl)bis(4,4,5,5-tetramethyl-1,3,2-dioxaborolane), 2,2'-(9-octyl-9H-carbazole-3,6-diyl)bis(1,3,2-dioxaborolane), 2,2'-(1,4-phenylene)bis(5,5-dimethyl-1,3,2-dioxaborinane), 2,2'-(2,5-dimethyl-1,4-phenylene)bis(1,3,2-dioxaborolane), 2,2'-(2-methyl-5-octyl-1,4-phenylene)bis(4,4,5,5-tetramethyl-1,3,2-dioxaborolane), 2,2'-(2,5-dibutyl-1,4-phenylene)bis(5,5-dimethyl-1,3,2-dioxaborinane), 2,2'-[2,5-bis(hexyloxy)-1,4-phenylene]bis(5,5-dimethyl-1,3,2-dioxaborinane), 2,5-bis(1,3,2-dioxaborolane-2-yl)thiophene, 2,5-bis(4,4,5,5-tetramethyl-1,3,2-dioxaborolane-2-yl)thiophene, 2,5-bis(1,3,2-dioxaborinane-2-yl)thiophene, 2,5-bis(5,5-dimethyl-1,3,2-dioxaborinane-2-yl)thiophene, 1,1'-bis(4,4,5,5-tetramethyl-1,3,2-dioxaborolane-2-yl)-4,4'-biphenyl, 1,1'-bis(1,3,2-dioxaborolane-2-yl)-4,4'-biphenyl, 1,1'-bis(1,3,2-dioxaborinane-2-yl)-4,4'-biphenyl, 1,1'-bis(5,5-dimethyl-1,3,2-dioxaborinane-2-yl)-4,4'-biphenyl and 5,5'-bis(4,4,5,5-tetramethyl-1,3,2-dioxaborolane-2-yl)-2,2'-bithiopene.

Of them, 2,2'-(9,9-dihexyl-9H-fluorene-2,7-diyl)bis(4,4,5,5-tetramethyl-1,3,2-dioxaborolane), 2,2'-(9,9-dioctyl-9H-fluorene-2,7-diyl)bis(4,4,5,5-tetramethyl-1,3,2-dioxaborolane), 2,2'-(9,9-didodecyl-9H-fluorene-2,7-diyl)bis(4,4,5,5-tetramethyl-1,3,2-dioxaborolane), 2,2'-(3,5-dimethoxy-9,9-dihexyl-9H-fluorene-2,7-diyl)bis(4,4,5,5-tetramethyl-1,3,2-dioxaborolane), 2,2'-(2-methyl-5-octyl-1,4-phenylene)bis(4,4,5,5-tetramethyl-1,3,2-dioxaborolane), 2,5-bis(4,4,5,5-tetramethyl-1,3,2-dioxaborolane-2-yl)thiophene, 1,1'-bis(4,4,5,5-tetramethyl-1,3,2-dioxaborolane-2-yl)-4,4'-biphenyl and 5,5'-bis(4,4,5,5-tetramethyl-1,3,2-dioxaborolane-2-yl)-2,2'-bithiopene are preferable.

In the production method of the present invention, two or more compounds represented by the formula (A) may be used in combination.

$X^2$ in the above-described formula (B) includes a chlorine atom, a bromine atom, an iodine atom, an alkylsulfonyloxy group, a fluorine-substituted alkylsulfonyloxy group or an arylsulfonyloxy group. Such $X^2$ links to a monovalent or divalent aromatic hydrocarbon group.

"Alkylsulfonyloxy group" includes a methanesulfonyloxy group and the like.

"Fluorine-substituted alkylsulfonyloxy group" includes a trifluoromethanesulfonyloxy group and the like.

"Arylsulfonyloxy group" includes a p-toluenesulfonyloxy group and the like.

The compound represented by the formula (B-1) includes phenyl bromide, o-tolyl bromide, m-tolyl bromide, p-tolyl bromide, 4-tert-butylphenyl bromide, 2,6-dimethylphenyl bromide, 2,4-dimethylphenyl bromide, 3,5-dimethylphenyl bromide, 2-(2-hydroxyethyl)phenyl bromide, 4-cyclohexylphenyl bromide, 3-bromobenzo trifluoride, 3-bromo-4-chlorobenzo trifluoride, 2-naphthyl bromide, 9-bromoanthracene, 9,10-dibromoanthracene, m-methoxyphenyl bromide, 4-bromobenzaldehyde, methyl 2-bromophenylacetate, methyl 3-bromophenylacetate, ethyl 4-bromophenylacetate, methyl 3-bromocinnamate, methyl 5-bromosalicylate, 4-bromobenzamide, 4-bromobenzonitrile, 9-bromophenanthrene, 2-bromofluorene, 5-bromoindanone, 6-bromo-2-naphthol, 2-pyridyl bromide, 2-bromofuran, 3-bromofuran, 2-bromothiophene, 4-bromopyrazole, 2-bromothiazole, 2-methyl-5-bromobenzothiazole, 5-bromouracil, 8-bromoquinoline, 4-bromoisoquinoline, 1-benzyl-5-bromotetrazole, phenyl chloride, o-tolyl chloride, 4-tert-butylphenyl chloride, 3-chlorotoluene, 4-chlorotoluene, 2,6-dimethylphenyl chloride, 3,5-dimethylphenyl chloride, 4-cyclohexyl chloride, 2-chloroacetophenone, 4-chloroacetophenone, 2-chloro-4-fluorotoluene, methyl 2-chlorophenylacetate, methyl 3-chlorophenylacetate, ethyl 4-chlorophenylacetate, 3-chlorobenzophenone, 4-chloro-1-naphthol, 4-chloro-N,N-dimethylaniline, 4-chloro-N,N-diphenylaniline, 5-chloro-N,N-dimethylaniline, 5-chloro-2-methoxyaniline, methyl 2-chlorobenzoate, ethyl 4-chlorobenzoate, phenyl 2-chlorobenzoate, N-(2-chlorophenyl)acetamide, N-(4-chlorophenyl)acetamide, 2-chlorobenzyl cyanide, 1-naphthyl chloride, 2-naphthyl chloride, 9-chloroanthracene, 2-methoxyphenyl chloride, 3-methoxyphenyl chloride, 4-methoxyphenyl chloride, 3,5-dimethoxy-2-chlorotoluene, 3-chlorobenzonitrile, 2-chloro-3-morpholino-1,4-naphthoquinone, 3-chlorobenzaldehyde, 2-pyridyl chloride, 2-chloro-6-trifluoropyridine, 2-chloro-3-picoline, 1-(3-chlorophenyl)-3-methyl-2-pyrazolin-5-one, 3-chlorothiophene, 2-chloro-3-methylthiophene, 5-chloro-1-methylimidazole, 5-chloro-1-methylbenzotriazole, 5-chloro-1-phenyl-1H-tetrazole, 4-chloro-1-methylindole, 2-chlorobenzoimidazole, 8-chloro-5-methoxyquinoline, 2-chlorobenzooxazole, 2-methyl-5-chlorobenzooxazole, 2-chlorobenzothiazole, 2-methyl-5-chlorobenzothiazole, 6-chloro-9-methyl-9H-purine, 2-chloropyrazine, phenyl iodide, o-tolyl iodide, 4-tert-butylphenyl iodide, 2,6-dimethylphenyl iodide, 3,5-dimethylphenyl iodide, 4-iodoacetophenone, ethyl 2-iodobenzoate, 2-naphthyl iodide, 9-iodoanthracene, 3-methoxyphenyl iodide, N-tert-butoxycarbonyl-4-iodophenylalanine methyl ester, 2-methyl-5-iodobenzooxazole, 2-methyl-5-iodobenzothiazole, 2-pyridyl iodide, 2-methyl-5-(p-toluenesulfonyloxy)benzooxazole, phenyl trifluoromethane sulfonate, 4-methylphenyl trifluoromethane sulfonate, 2,6-dimethylphenyl trifluoromethane sulfonate, 2-methane sulfonate, 2-methyl-5-(trifluoromethanesulfonyloxy)benzothiazole and the like.

The compound represented by the formula (B-2) includes 2,7-dibromo-9,9-dihexyl-9H-fluorene, 2,7-dibromo-9,9-dioctyl-9H-fluorene, 2,7-dibromo-9,9-didodecyl-9H-fluorene, 2,7-dichloro-9,9-dihexyl-9H-fluorene, 2,7-dichloro-9,9-dioctyl-9H-fluorene, 2,7-dichloro-9,9-didodecyl-9H-fluorene, 2-bromo-7-chloro-9,9-dihexyl-9H-fluorene, 2-bromo-7-chloro-9,9-dioctyl-9H-fluorene, 2-bromo-7-chloro-9,9-didodecyl-9H-fluorene, 1,4-dibromobenzene, 1,3-dibromobenzene, 1,4-dibromo-2-ethylbenzene, 1,4-dibromo-2-methoxybenzene, dimethyl 2,5-dibromo terephthalate, 1,4-dibromonaphthalene, 3,5-dibromopyridine, 1,1'-dibromo-4,4'-biphenyl, 2,5-dibromopyridine, 1,4-dibromo-2,5-dihexyloxybenzene, 1-bromo-4-chlorobenzene, 1-bromo-4-chlorotoluene, 1-bromo-4-chloro-2-propylbenzene, 2,5-dibromo-4'-phenoxybenzophenone, 2,5-dibromo-3-hexylthiophene, 2,5-dibromo-3,2,5-dibromo-3-octylthiophene-dodecylthiophene, 2,5-dichloro-3-hexylthiophene, 5,5'-dibromo-2,2'-bithiophene, 5,5'-dibromo-3,3'-dihexyl-2,2'-bithiophene, bis(4-bromophenyl)-4-(4-t-butyl)benzeneamine, bis(4-bromophenyl)-4-(1-methylpropyl)benzeneamine, bis(4-bromophenyl)-4-benzeneamine, N,N'-bis(4-bromophenyl)-N,N'-bis(4-n-butylphenyl)-1,4-benzenediamine, N,N'-bis(4-bromophenyl)-bicyclo[4,2,0]octa-1,3,5-triene-3-amine, N,N'-bis(4-bromophenyl)-N,N'-bis(4-butylphenyl)-1,4-benzenediamine, N,N'-bis(4-bromophenyl)-N,N'-bis[4-(1,1-dimethylethyl)-2,6-dimethylphenyl]-1,4-benzenediamine, 4,7-dibromo-2,1,3-benzothiadiazole, 4,7-dibromo-2,1,3-benzoselenadiazole, 4,7-bis(5-bromo-2-thienyl)-2,1,3-benzothiadiazole, 4,7-bis(5-bromo-4-methyl-2-thienyl)-2,1,3-benzothiadiazole, 4,7-bis(5-bromo-3-methyl-2-thienyl)-2,1,3-benzothiadiazole, 3,7-dibromo-10-(4-n-butylphenyl)-10H-phenothiazine, 3,7-dibromo-10-(4-n-butylphenyl)-10H-phenoxazine, 3,3'-[1,1'-biphenyl]-4,4'-diylbis[[4-bromophenyl]imino]]bisbenzoic acid diethyl ester and 4,4'-bis[(4-bromophenyl)phenylamino]biphenyl.

Of them, 2,7-dibromo-9,9-dihexyl-9H-fluorene, 2,7-dibromo-9,9-dioctyl-9H-fluorene, 2,7-dibromo-9,9-didodecyl-9H-fluorene, 1,4-dibromobenzene, 1,3-dibromobenzene, 2,5-dibromo-3-hexylthiophene and bis(4-bromophenyl)-4-benzeneamine are preferable.

In the production method of the present invention, two or more compounds represented by the formula (B) may be used in combination.

The use amount of the compound represented by the formula (B) is usually in the range of 0.8 mol to 1.2 mol, preferably in the range of 0.9 mol to 1.1 mol with respect to 1 mol of a compound represented by the formula (A).

<Base>

The base includes inorganic bases and organic bases.

The inorganic base includes alkali metal hydroxides, alkaline earth metal hydroxides, alkali metal carboxylic acid salts, alkaline earth metal carboxylic acid salts, alkali metal carbonates, alkaline earth metal carbonates, alkali metal hydrogen carbonates, alkaline earth metal hydrogen carbonates, alkali metal phosphates and alkaline earth metal phosphates, and alkali metal carbonates and alkali metal phosphates are preferable.

Specific examples of the inorganic base include lithium hydroxide, sodium hydroxide, potassium hydroxide, cesium hydroxide, calcium hydroxide, barium hydroxide, sodium formate, potassium formate, calcium formate, sodium acetate, potassium acetate, sodium carbonate, potassium carbonate, cesium carbonate, calcium carbonate, sodium hydrogen carbonate, potassium hydrogen carbonate, sodium phosphate and potassium phosphate, and sodium carbonate, potassium carbonate, cesium carbonate, sodium phosphate and potassium phosphate are preferable.

The organic base includes alkylammonium hydroxides, alkylammonium carbonates, alkylammonium bicarbonates, alkylammonium boronic acid salts, 1,5-diazabicyclo[4.3.0]non-5-ene (DBN), 1,8-diazabicyclo[5.4.0]undec-7-ene (DBU), 1,4-diazabicyclo[2.2.2]octane (DABCO), dimethylaminopyridine (DMAP), pyridine, trialkylamine, and alkylammonium fluorides such as tetraalkylammonium fluoride and the like. Of them, tetraalkylammonium hydroxides such as tetramethylammonium hydroxides, tetraethylammonium hydroxides, tetra-n-propylammonium hydroxides and the like are preferable.

The use amount of the base is usually in the range of 0.5 equivalent to 20 equivalent, preferably in the range of 0.5 equivalent to 6 equivalent. Here, the equivalent signifies the ratio of the theoretical substance amount of a base necessary for neutralizing hydrogen ions equivalent to the total substance amount of $X^2$ contained in a compound represented by the formula (B) to the total substance amount of $X^2$ contained in a compound represented by the formula (B).

<Phase Transfer Catalyst>

When an inorganic base is used as the base in the production method of the present invention, a phase transfer catalyst may also be used together. The phase transfer catalyst includes tetraalkyl ammonium halide, tetraalkylammonium hydrogen sulfate and tetraalkylammonium hydroxide. Tetraalkylammonium halides such as tricaprylmethylammonium chloride (available as Aliquat (registered trademark) 336 from Sigma-Aldrich) and the like are preferable.

The use amount of the phase transfer catalyst is usually in the range of 0.001 equivalent to 1 equivalent, preferably in the range of 0.01 equivalent to 0.5 equivalent. Here, the equivalent signifies the ratio to the total substance amount of $X^2$ contained in a compound represented by the formula (B).

<Aprotic Organic Solvent>

"Aprotic organic solvent" denotes an organic solvent not having a group having active hydrogen such as a hydroxyl group (—OH), an amino group, a carboxyl group (—COOH) and the like in its molecule and capable of dissolving a compound represented by the formula (A) and a compound represented by the formula (B).

The aprotic organic solvent includes ether solvents such as an acyclic ether solvent, a cyclic ether solvent and the like, aprotic polar solvents, aromatic hydrocarbon solvents and aliphatic hydrocarbon solvents, and ether solvents, aromatic hydrocarbon solvents and aliphatic hydrocarbon solvents are preferable. The aprotic polar solvent includes N-methylpyrrolidone, N,N-dimethylformamide, N,N-dimethylacetamide, dimethyl sulfoxide and acetonitrile. The acyclic ether solvent includes diethyl ether, diisopropyl ether, ethylene glycol dimethyl ether and diethylene glycol dimethyl ether. The cyclic ether solvent includes 1,4-dioxane and tetrahydrofuran. The aromatic hydrocarbon solvent includes benzene, toluene, xylene and mesitylene. The aliphatic hydrocarbon solvent includes hexane, heptane and cyclohexane.

Preferable from the standpoint of the solubility of a compound represented by the formula (A) and a compound represented by the formula (B) are toluene, xylene, mesitylene, diethyl ether, diisopropyl ether, ethylene glycol dimethyl ether, diethylene glycol dimethyl ether, 1,4-dioxane and tetrahydrofuran. If necessary, two or more aprotic organic solvents may be used in combination, and specific examples thereof include a mixed solvent of tetrahydrofuran and toluene and a mixed solvent of ethylene glycol dimethyl ether and toluene.

<Palladium Compound>

The palladium compound is a compound in which an atom other than palladium is linked to palladium, and includes preferably a palladium(0) complex and a palladium(II) complex.

The palladium(0) complex includes a complex in which dibenzylideneacetone is coordinated to 0-valent palladium, what is called a dibenzylideneacetone-palladium(0) complex. Specific examples thereof include tris(dibenzylideneacetone)dipalladium(0), tris(dibenzylideneacetone)dipalladium(0) chloroform adduct and bis(dibenzylideneacetone)palladium(0).

The palladium(II) complex includes palladiumcarboxylic acid salts such as palladium(II) acetate, palladium(II) trifluoroacetate, palladium(II) acetylacetonate and the like, palladium halides such as palladium(II) chloride, palladium(II) bromide, palladium(II) iodide and the like, and palladium halide complexes such as allylpalladium(II) chloride dimer, bis(2-methylallyl)palladium(II) chloride dimer, dichloro(1,5-cyclooctadiene)palladium(II), dichlorobis(acetonitrile)palladium(II), dichlorobis(benzonitrile)palladium(II) and the like. Of them, tris(dibenzylideneacetone)dipalladium(0), bis(dibenzylideneacetone)palladium(0), palladium(II) chloride, palladium(II) bromide and palladium(II) acetate are preferable.

The use amount of the palladium compound is usually in the range of 0.00001 mol to 0.8 mol, preferably in the range of 0.00002 mol to 0.2 mol with respect to 1 mol of a compound represented by the formula (B).

Phosphine Represented by the Formula (C)

The phosphine represented by the formula (C) is represented by the following formula (C).

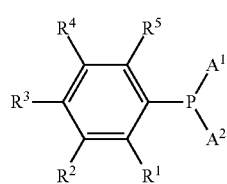

(C)

In the formula (C), $A^1$ and $A^2$ represent each independently a cyclopentyl group which may have a substituent. The cyclopentyl group which may have a substituent is preferably a cyclopentyl group which may have an alkyl group having a number of carbon atoms of 1 to 20 or an aryl group having a number of carbon atoms of 6 to 20 as a substituent, more preferably a cyclopentyl group.

$A^1$ and $A^2$ may be the same or different. Preferably, $A^1$ and $A^2$ are the same.

The alkyl group having a number of carbon atoms of 1 to 20 includes a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group, and an alkyl group having a number of carbon atoms of 1 to 6 is preferable, a tert-butyl group is more preferable.

The aryl group having a number of carbon atoms of 6 to 20 includes a phenyl group, a 4-methylphenyl group, a 2-methylphenyl group, a 1-naphthyl group, a 2-naphthyl group, a 3-phenanthryl group and a 2-anthryl group.

In the formula (C), $R^2$, $R^3$ and $R^4$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20.

The alkyl group having a number of carbon atoms of 1 to 20 includes a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group, and an alkyl group having a number of carbon atoms of 1 to 6 is preferable, an alkyl group having a number of carbon atoms of 1 to 4 is more preferable.

The cycloalkyl having a number of carbon atoms of 3 to 20 includes a cyclohexyl group, a cycloheptyl group, a cyclooctyl group and a cyclononyl group, and a cycloalkyl group having a number of carbon atoms of 3 to 8 is preferable.

The fluoroalkyl group having a number of carbon atoms of 1 to 20 includes a monofluoromethyl group, a difluoromethyl group, a trifluoromethyl group, a 2,2,2-trifluoroethyl group, a pentafluoroethyl group, a perfluoro-n-propyl group and a perfluoroisopropyl group, and a fluoroalkyl group having a number of carbon atoms of 1 to 6 is preferable.

The alkoxy group having a number of carbon atoms of 1 to 20 includes a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-icosyloxy group, and an alkoxy group having a number of carbon atoms of 1 to 6 is preferable, an alkoxy group having a number of carbon atoms of 1 to 4 is more preferable.

The cycloalkoxy group having a number of carbon atoms of 3 to 20 includes a cyclopentyloxy group and a cyclohexyloxy group, and a cycloalkoxy group having a number of carbon atoms of 3 to 8 is preferable.

The fluoroalkoxy group having a number of carbon atoms of 1 to 20 includes a monofluoromethoxy group, a difluoromethoxy group, a trifluoromethoxy group, a 2,2,2-trifluoroethoxy group, a pentafluoroethoxy group, a perfluoro-n-propoxy group and a perfluoroisopropoxy group, and a fluoroalkoxy group having a number of carbon atoms of 1 to 6 is preferable.

The aryl group having a number of carbon atoms of 6 to 20 includes a phenyl group, a 4-methylphenyl group, a 2-methylphenyl group, a 1-naphthyl group, a 2-naphthyl group, a 3-phenanthryl group and a 2-anthryl group.

The aryloxy group having a number of carbon atoms of 6 to 20 includes a phenoxy group, a 4-methylphenoxy group, a 2-methylphenoxy group, a 1-naphthyloxy group, a 2-naphthyloxy group, a 3-phenanthryloxy group and a 2-anthryloxy group.

It is preferable that $R^2$, $R^3$ and $R^4$ represent each independently a hydrogen atom, a fluorine atom, an alkyl group having a number of carbon atoms of 1 to 20, an alkoxy group having a number of carbon atoms of 1 to 20 or a fluoroalkoxy group having a number of carbon atoms of 1 to 20, it is more preferable that $R^2$, $R^3$ and $R^4$ represent each independently a hydrogen atom, a fluorine atom, an alkyl group having a number of carbon atoms of 1 to 6 or an alkoxy group having a number of carbon atoms of 1 to 6. It is preferable that any one of $R^2$, $R^3$ and $R^4$ represents a fluorine atom, an alkyl group having a number of carbon atoms of 1 to 6 or an alkoxy group having a number of carbon atoms of 1 to 6 and the remaining two represent a hydrogen atom. It is particularly preferable that $R^2$, $R^3$ and $R^4$ represent a hydrogen atom.

In the formula (C), $R^1$ and $R^5$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20, an aryloxy group having a number of carbon atoms of 6 to 20, a group represented by the formula (D):

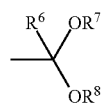

(wherein, $R^6$ represents a hydrogen atom, an alkyl group having a number of carbon atoms of 1 to 20 or a cycloalkyl group having a number of carbon atoms of 3 to 20, $R^7$ and $R^8$ represent each independently an alkyl group having a number of carbon atoms of 1 to 20 or a cycloalkyl group having a number of carbon atoms of 3 to 20, and $R^7$ and $R^8$ may be linked to form a ring.) or a group represented by the formula (E):

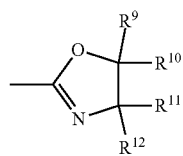

(wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20.).

The alkyl group having a number of carbon atoms of 2 to 20 includes an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group, and an alkyl group having a number of carbon atoms of 2 to 6 is preferable, an alkyl group having a number of carbon atoms of 2 to 4 is more preferable.

The cycloalkyl group having a number of carbon atoms of 3 to 20 includes the same groups as described above, and a cycloalkyl group having a number of carbon atoms of 3 to 8 is preferable.

The fluoroalkyl group having a number of carbon atoms of 1 to 20 includes the same groups as described above, and a fluoroalkyl group having a number of carbon atoms of 1 to 6 is preferable.

The alkoxy group having a number of carbon atoms of 1 to 20 includes the same groups as described above, and an alkoxy group having a number of carbon atoms of 1 to 6 is preferable, an alkoxy group having a number of carbon atoms of 1 to 4 is more preferable.

The cycloalkoxy group having a number of carbon atoms of 3 to 20 includes the same groups as described above, and a cycloalkoxy group having a number of carbon atoms of 3 to 8 is preferable.

The fluoroalkoxy group having a number of carbon atoms of 1 to 20 includes the same groups as described above, and a fluoroalkoxy group having a number of carbon atoms of 1 to 6 is preferable.

The aryl group having a number of carbon atoms of 6 to 20 includes the same groups as described above.

The aryloxy group having a number of carbon atoms of 6 to 20 includes the same groups as described above.

The alkyl group having a number of carbon atoms of 1 to 20 represented by $R^6$ includes the same groups as described above, and an alkyl group having a number of carbon atoms of 1 to 6 is preferable. The cycloalkyl group having a number of carbon atoms of 3 to 20 represented by $R^6$ includes the same groups as described above, and a cycloalkyl group having a number of carbon atoms of 3 to 8 is preferable. The alkyl group having a number of carbon atoms of 1 to 20 represented by $R^7$ and $R^8$ includes the same groups as described above, and an alkyl group having a number of carbon atoms of 1 to 6 is preferable. The cycloalkyl group having a number of carbon atoms of 3 to 20 represented by $R^7$ and $R^8$ includes the same groups as described above, and a cycloalkyl group having a number of carbon atoms of 3 to 8 is preferable.

The group represented by the formula (D) includes groups shown below.

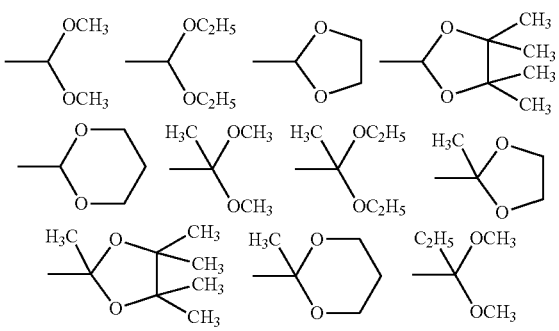

-continued

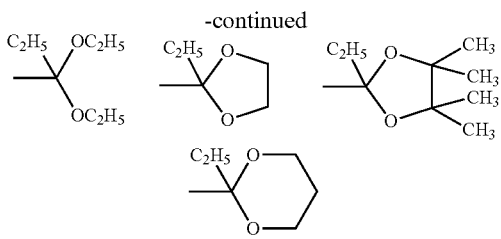

The alkyl group having a number of carbon atoms of 1 to 20 represented by $R^9$, $R^{10}$, $R^{11}$ and $R^{12}$ includes the same groups as described above, and an alkyl group having a number of carbon atoms of 1 to 6 is preferable. The cycloalkyl group having a number of carbon atoms of 3 to 20 represented by $R^9$, $R^{10}$, $R^{11}$ and $R^{12}$ includes the same groups as described above, and a cycloalkyl group having a number of carbon atoms of 3 to 8 is preferable. The aryl group having a number of carbon atoms of 6 to 20 represented by $R^9$, $R^{10}$, $R^{11}$ and $R^{12}$ includes the same groups as described above.

The group represented by the formula (E) includes groups shown below.

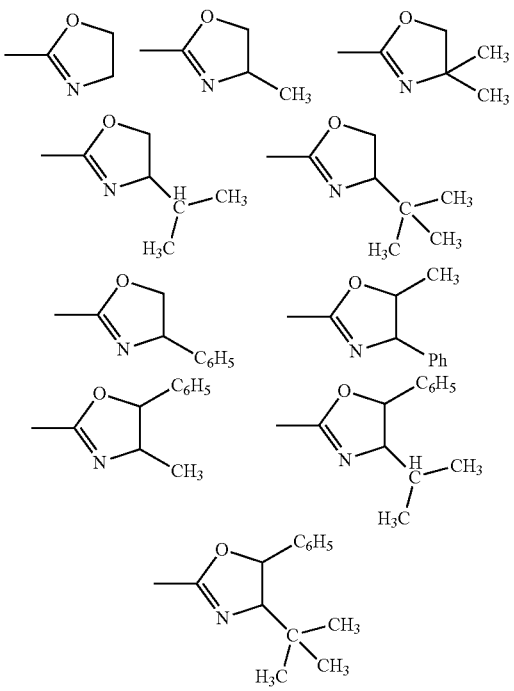

It is preferable that $R^1$ and $R^5$ represent each independently a hydrogen atom, a fluorine atom, an alkyl group having a number of carbon atoms of 2 to 20, an alkoxy group having a number of carbon atoms of 1 to 20 or an aryl group having a number of carbon atoms of 6 to 20. It is more preferable that $R^1$ and $R^5$ represent each independently a hydrogen atom, a fluorine atom, an alkyl group having a number of carbon atoms of 2 to 6, an alkoxy group having a number of carbon atoms of 1 to 6 or an aryl group having a number of carbon atoms of 6 to 14. It is particularly preferable that one of $R^1$ and $R^5$ represents a hydrogen atom or an alkoxy group having a number of carbon atoms of 1 to 6 and the other represents a hydrogen atom, an alkyl group having a number of carbon atoms of 2 to 6, an alkoxy group having a number of carbon atoms of 1 to 6 or an aryl group having a number of carbon atoms of 6 to 14. Further, it is preferable that at least one selected from $R^1$ and $R^5$ is an alkoxy group having a number of carbon atoms of 1 to 20.

Here, in the formula (C), all of $R^1$ to $R^5$ do not simultaneously represent a hydrogen atom. When at least one of $R^1$ to $R^5$ is a fluoroalkyl group having a number of carbon atoms of 1 to 20, at least one of the remaining $R^1$ to $R^5$ is not a hydrogen atom or a fluoroalkyl group having a number of carbon atoms of 1 to 20. Further, $R^2$ and $R^3$ may be linked to form a ring (for example, a benzene ring) together with a carbon atom to which they are linked, and $R^3$ and $R^4$ may be linked to form a ring (for example, a benzene ring) together with a carbon atom to which they are linked.

The phosphine represented by the formula (C) includes a phosphine represented by the formula (C) in which $A^1$ and $A^2$ represent a cyclopentyl group, $R^1$ represents a hydrogen atom and $R^5$ represents an alkoxy group having a number of carbon atoms of 1 to 6, a phosphine represented by the formula (C) in which $A^1$ and $A^2$ represent a cyclopentyl group, $R^1$ represents a hydrogen atom and $R^5$ represents an alkyl group having a number of carbon atoms of 2 to 6, a phosphine represented by the formula (C) in which $A^1$ and $A^2$ represent a cyclopentyl group, $R^1$ represents a hydrogen atom and $R^5$ represents an aryl group having a number of carbon atoms of 6 to 14, a phosphine represented by the formula (C) in which $A^1$ and $A^2$ represent a cyclopentyl group and $R^1$ and $R^5$ represent each independently an alkoxy group having a number of carbon atoms of 1 to 6, a phosphine represented by the formula (C) in which $A^1$ and $A^2$ represent a cyclopentyl group and $R^1$ and $R^5$ represent the same alkoxy group having a number of carbon atoms of 1 to 6, a phosphine represented by the formula (C) in which $A^1$ and $A^2$ represent a cyclopentyl group, any one of $R^2$, $R^3$ and $R^4$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (C) in which $A^1$ and $A^2$ represent a cyclopentyl group, $R^1$ represents a hydrogen atom, $R^5$ represents an alkoxy group having a number of carbon atoms of 1 to 6, any one of $R^2$, $R^3$ and $R^4$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (C) in which $A^1$ and $A^2$ represent a cyclopentyl group, $R^1$ represents a hydrogen atom, $R^5$ represents an alkoxy group having a number of carbon atoms of 1 to 6 and all of $R^2$, $R^3$ and $R^4$ represent a hydrogen atom, a phosphine represented by the formula (C) in which $A^1$ and $A^2$ represent a cyclopentyl group, $R^1$ represents a hydrogen atom, $R^5$ represents an alkyl group having a number of carbon atoms of 2 to 6, any one of $R^2$, $R^3$ and $R^4$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (C) in which $A^1$ and $A^2$ represent a cyclopentyl group, $R^1$ represents a hydrogen atom, $R^5$ represents an alkyl group having a number of carbon atoms of 2 to 6 and all of $R^2$, $R^3$ and $R^4$ represent a hydrogen atom, a phosphine represented by the formula (C) in which $A^1$ and $A^2$ represent a cyclopentyl group, $R^1$ and $R^5$ represent each independently an alkoxy group having a number of carbon atoms of 1 to 6, any one of $R^2$, $R^3$ and $R^4$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (C) in which $A^1$ and $A^2$ represent a cyclopentyl group, $R^1$ and $R^5$ represent each independently an alkoxy group having a number of carbon atoms of 1 to 6 and all of $R^2$, $R^3$ and $R^4$ represent a hydrogen atom, a phosphine represented by the formula (C) in which $A^1$ and $A^2$ represent a cyclopentyl group, $R^1$ and $R^5$ represent the same alkoxy group having a number of carbon atoms of 1 to 6, any one of $R^2$, $R^3$ and $R^4$ represents a fluorine atom, an alkyl group having a number of carbon atoms of 1 to 6 or an alkoxy group having a number of carbon atoms of 1 to 6 and the remaining two represent a hydrogen atom and a phosphine represented by the formula (C) in which $A^1$ and $A^2$ represent a cyclopentyl group, $R^1$ and $R^5$ represent the same alkoxy group having a number of carbon atoms of 1 to 6 and all of $R^2$, $R^3$ and $R^4$ represent a hydrogen atom.

Specific examples of the phosphine represented by the formula (C) include dicyclopentyl(4-fluorophenyl)phosphine, dicyclopentyl(3-fluorophenyl)phosphine, dicyclopentyl(2-fluorophenyl)phosphine, dicyclopentyl(4-methylphenyl)phosphine, dicyclopentyl(3-methylphenyl)phosphine, dicyclopentyl(4-ethylphenyl)phosphine, dicyclopentyl(3-ethylphenyl)phosphine, dicyclopentyl(2-ethylphenyl)phosphine, dicyclopentyl(4-isopropylphenyl)phosphine, dicyclopentyl(3-isopropylphenyl)phosphine, dicyclopentyl(2-isopropylphenyl)phosphine, dicyclopentyl(4-tert-butylphenyl)phosphine, dicyclopentyl(3-tert-butylphenyl)phosphine, dicyclopentyl(4-methoxyphenyl)phosphine, dicyclopentyl(3-methoxyphenyl)phosphine, dicyclopentyl(2-methoxyphenyl)phosphine, dicyclopentyl(4-ethoxyphenyl)phosphine, dicyclopentyl(3-ethoxyphenyl)phosphine, dicyclopentyl(2-ethoxyphenyl)phosphine, dicyclopentyl(4-trifluoromethoxyphenyl)phosphine, dicyclopentyl(3-trifluoromethoxyphenyl)phosphine, dicyclopentyl(2-trifluoromethoxyphenyl)phosphine, dicyclopentyl(4-pentafluoroethoxyphenyl)phosphine, dicyclopentyl(3-pentafluoroethoxyphenyl)phosphine, dicyclopentyl(2-pentafluoroethoxyphenyl)phosphine, dicyclopentyl([1,1'-biphenyl]-4-yl)phosphine, dicyclopentyl([1,1'-biphenyl]-3-yl)phosphine, dicyclopentyl([1,1'-biphenyl]-2-yl)phosphine, dicyclopentyl(4-phenoxyphenyl)phosphine, dicyclopentyl(3-phenoxyphenyl)phosphine, dicyclopentyl(2-phenoxyphenyl)phosphine, dicyclopentyl(4-fluoro-2-methoxyphenyl)phosphine, dicyclopentyl(2,4-dimethoxyphenyl)phosphine, dicyclopentyl(2,6-dimethoxyphenyl)phosphine, dicyclopentyl(4-trifluoromethyl-2-methoxyphenyl)phosphine, and, dicyclopentyl(2-naphthyl)phosphine, 2-[2-(dicyclopentylphosphino)phenyl]-4,5-dihydrooxazole, 2-[2-(dicyclopentylphosphino)phenyl]-4,5-dihydro-4-methyloxazole, 2-[2-(dicyclopentylphosphino)phenyl]-4,5-dihydro-4-isopropyloxazole, 2-[2-(dicyclopentylphosphino)phenyl]-4,5-dihydro-4-tert-butyloxazole, 2-[2-(dicyclopentylphosphino)phenyl]-4,5-dihydro-4-phenyloxazole, dicyclopentyl(2-(dimethoxymethyl)phenyl)phosphine, dicyclopentyl(2-(diethoxymethyl)phenyl)phosphine, dicyclopentyl(2-(1,3-dioxolane-2-yl)phenyl)phosphine, dicyclopentyl(2-(4,4,5,5-tetramethyl-1,3-dioxolane-2-yl)phenyl)phosphine, dicyclopentyl(2-(1,3-dioxane-2-yl)phenyl)phosphine, dicyclopentyl(2-(1,1-dimethoxyethyl)phenyl)phosphine, dicyclopentyl(2-(2-methyl-1,3-dioxolane-2-yl)phenyl)phosphine, dicyclopentyl(2-(2-methyl-4,4,5,5-tetramethyl-1,3-dioxolane-2-yl)phenyl)phosphine and dicyclopentyl(2-(2-methyl-1,3-dioxane-2-yl)phenyl)phosphine.

Phosphonium Salt Represented by the Formula (F)

The phosphonium salt represented by the formula (F) is represented by the following formula (F).

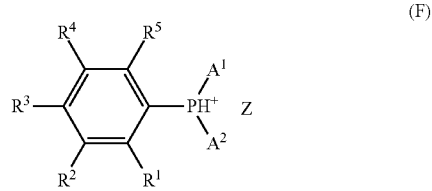

(F)

In the formula (F), $A^1$, $A^2$, $R^1$ to $R^5$ represent the same meaning as described above, and Z represents an anion.

The anion represented by Z includes halogen ions such as $F^-$, $Cl^-$, $Br^-$ and $I^-$, a perchlorate ion, a hydrogen sulfate ion, a hexafluorophosphate ion, an anion represented by the formula (Y):

(Y)

(wherein, $R^6$ represents an aryl group which may have a substituent, a monovalent aromatic heterocyclic group which may have a substituent, or a halogen atom.)
and the like, and an anion represented by the formula (Y) is preferable.

The aryl group which may have a substituent represented by $R^{60}$ includes a phenyl group, a 4-methylphenyl group, a 3-methylphenyl group, a 2-methylphenyl group, a 4-tert-butylphenyl group, a 4-fluorophenyl group, a pentafluorophenyl group and the like, preferably includes a phenyl group, a 4-methylphenyl group, a 4-fluorophenyl group and a pentafluorophenyl group, more preferably includes a phenyl group.

The monovalent aromatic heterocyclic group which may have a substituent represented by $R^{60}$ includes a 2-pyridyl group, a 3-pyridyl group, a 4-pyridyl group, a 4-tert-butyl-2-pyridyl group, a 2-thiophenyl group and the like, preferably includes a 2-pyridyl group, a 3-pyridyl group and a 4-pyridyl group, more preferably includes a 4-pyridyl group.

The halogen atom represented by $R^{60}$ includes a fluorine atom, a chlorine atom, a bromine atom and an iodine atom, preferably includes a fluorine atom.

As $R^{60}$, a phenyl group and a fluorine atom are particularly preferable, a fluorine atom is most preferable, among the above-described examples.

Specific examples of the phosphonium salt represented by the formula (F) include dicyclopentyl(4-fluorophenyl)phosphonium tetrafluoroborate, dicyclopentyl(3-fluorophenyl)phosphonium tetrafluoroborate, dicyclopentyl(2-fluorophenyl)phosphonium tetrafluoroborate, dicyclopentyl(4-methylphenyl)phosphonium tetrafluoroborate, dicyclopentyl(3-methylphenyl)phosphonium tetrafluoroborate, dicyclopentyl(4-ethylphenyl)phosphonium tetrafluoroborate, dicyclopentyl(3-ethylphenyl)phosphonium tetrafluoroborate, dicyclopentyl(2-ethylphenyl)phosphonium tetrafluoroborate, dicyclopentyl(4-isopropylphenyl)phosphonium tetrafluoroborate, dicyclopentyl(3-isopropylphenyl)phosphonium tetrafluoroborate, dicyclopentyl(2-isopropylphenyl)phosphonium tetrafluoroborate, dicyclopentyl(4-tert-butylphenyl)phosphonium tetrafluoroborate, dicyclopentyl(3-tert-butylphenyl)phosphonium tetrafluoroborate, dicyclopentyl(4-methoxyphenyl)phosphonium tetrafluoroborate, dicyclopentyl(3-methoxyphenyl)phosphonium tetrafluoroborate, dicyclopentyl(2-methoxyphenyl)phosphonium tetrafluoroborate, dicyclopentyl(4-ethoxyphenyl)phosphonium tetrafluoroborate, dicyclopentyl(3-ethoxyphenyl)phosphonium tetrafluoroborate, dicyclopentyl(2-ethoxyphenyl)phosphonium tetrafluoroborate, dicyclopentyl(4-trifluoromethoxyphenyl)phosphonium tetrafluoroborate, dicyclopentyl(3-trifluoromethoxyphenyl)phosphonium tetrafluoroborate, dicyclopentyl(2-trifluoromethoxyphenyl)phosphonium tetrafluoroborate, dicyclopentyl(4-pentafluoroethoxyphenyl)phosphonium tetrafluoroborate, dicyclopentyl(3-pentafluoroethoxyphenyl)phosphonium tetrafluoroborate, dicyclopentyl(2-pentafluoroethoxyphenyl)phosphonium tetrafluoroborate, dicyclopentyl([1,1'-biphenyl]-4-yl)phosphonium tetrafluoroborate, dicyclopentyl([1,1'-biphenyl]-3-yl)phosphonium tetrafluoroborate, dicyclopentyl([1,1'-biphenyl]-2-yl)phosphonium tetrafluoroborate, dicyclopentyl(4-phenoxyphenyl)phosphonium tetrafluoroborate, dicyclopentyl(3-phenoxyphenyl)phosphonium tetrafluoroborate, dicyclopentyl(2-phenoxyphenyl)phosphonium tetrafluoroborate, dicyclopentyl(4-fluoro-2-methoxyphenyl)phosphonium tetrafluoroborate, dicyclopentyl(2,4-dimethoxyphenyl)phosphonium tetrafluoroborate, dicyclopentyl(2,6-dimethoxyphenyl)phosphonium tetrafluoroborate, dicyclopentyl(4-trifluoromethyl-2-methoxyphenyl)phosphonium tetrafluoroborate and dicyclopentyl(2-naphthyl)phosphonium tetrafluoroborate, dicyclopentyl(2-(dimethoxymethyl)phenyl)phosphonium tetrafluoroborate, dicyclopentyl(2-(diethoxymethyl)phenyl)phosphonium tetrafluoroborate, dicyclopentyl(2-(1,3-dioxolane-2-yl)phenyl)phosphonium tetrafluoroborate, dicyclopentyl(2-(4,4,5,5-tetramethyl-1,3-dioxolane-2-yl)phenyl)phosphonium tetrafluoroborate, dicyclopentyl(2-(1,3-dioxane-2-yl)phenyl)phosphonium tetrafluoroborate, dicyclopentyl(2-(1,1-dimethoxyethyl)phenyl)phosphonium tetrafluoroborate, dicyclopentyl(2-(2-methyl-1,3-dioxolane-2-yl)phenyl)phosphonium tetrafluoroborate, dicyclopentyl(2-(2-methyl-4,4,5,5-tetramethyl-1,3-dioxolane-2-yl)phenyl)phosphonium tetrafluoroborate and dicyclopentyl(2-(2-methyl-1,3-dioxane-2-yl)phenyl)phosphonium tetrafluoroborate, dicyclopentyl(2-methoxyphenyl)phosphonium tetraphenyl borate, dicyclopentyl(2-ethoxyphenyl)phosphonium tetraphenyl borate, dicyclopentyl(4-fluoro-2-methoxyphenyl)phosphonium tetraphenyl borate, dicyclopentyl(2,4-dimethoxyphenyl)phosphonium tetraphenyl borate, dicyclopentyl(2,6-dimethoxyphenyl)phosphonium tetraphenyl borate, dicyclopentyl(4-trifluoromethyl-2-methoxyphenyl)phosphonium tetraphenyl borate, dicyclopentyl(2-methoxyphenyl)phosphonium tetramesitylborate, dicyclopentyl(2-ethoxyphenyl)phosphonium tetramesityl borate, dicyclopentyl(4-fluoro-2-methoxyphenyl)phosphonium tetramesityl borate, dicyclopentyl(2,4-dimethoxyphenyl)phosphonium tetramesityl borate, dicyclopentyl(2,6-dimethoxyphenyl)phosphonium tetramesityl borate and dicyclopentyl(4-trifluoromethyl-2-methoxyphenyl)phosphonium tetramesityl borate.

Phosphine Represented by the Formula (G)

The phosphine represented by the formula (C) is preferably a phosphine represented by the following formula (G).

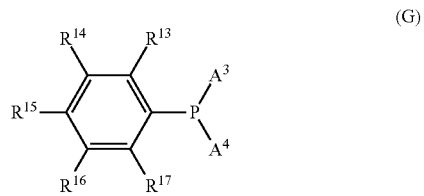

In the formula (G), $A^3$ and $A^4$ represent each independently a cyclopentyl group which may have a substituent. The cyclopentyl group which may have a substituent is preferably a cyclopentyl group which may have an alkyl group having a number of carbon atoms of 1 to 20 or an aryl group having a number of carbon atoms of 6 to 20 as a substituent, more preferably a cyclopentyl group.

$A^3$ and $A^4$ may be the same or different. Preferably, $A^3$ and $A^4$ are the same.

The alkyl group having a number of carbon atoms of 1 to 20 and the aryl group having a number of carbon atoms of 6 to 20 include the same groups as described above.

In the formula (G), $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the above-described formula (E).

The alkyl group having a number of carbon atoms of 2 to 20, the cycloalkyl group having a number of carbon atoms of 3 to 20, the fluoroalkyl group having a number of carbon atoms of 1 to 20, the alkoxy group having a number of carbon atoms of 1 to 20, the cycloalkoxy group having a number of carbon atoms of 1 to 20, the fluoroalkoxy group having a number of carbon atoms of 1 to 20, the aryloxy group having a number of carbon atoms of 6 to 20 and the group represented by the formula (E) include the same groups as described above.

It is preferable that $R^{13}$ and $R^{17}$ represent each independently a hydrogen atom, a fluorine atom, an alkyl group having a number of carbon atoms of 2 to 6, an alkoxy group having a number of carbon atoms of 1 to 6, a cycloalkoxy group having a number of carbon atoms of 3 to 8 or a fluoroalkoxy group having a number of carbon atoms of 1 to 6. It is more preferable that $R^{13}$ and $R^{17}$ represent each independently a hydrogen atom, an alkyl group having a number of carbon atoms of 2 to 6 or an alkoxy group having a number of carbon atoms of 1 to 6. It is particularly preferable that one of $R^{13}$ and $R^{17}$ represents a hydrogen atom or an alkoxy group having a number of carbon atoms of 1 to 6 and the other represents a hydrogen atom, an alkyl group having a number of carbon atoms of 2 to 6 or an alkoxy group having a number of carbon atoms of 1 to 6. Further, it is preferable that at least one selected from $R^{13}$ and $R^{17}$ is an alkoxy group having a number of carbon atoms of 1 to 20.

In the formula (G), $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20. The alkyl group having a number of carbon atoms of 1 to 20, the cycloalkyl group having a number of carbon atoms of 3 to 20, the fluoroalkyl group having a number of carbon atoms of 1 to 20, the alkoxy group having a number of carbon atoms of 1 to 20, the cycloalkoxy group having a number of carbon atoms of 3 to 20, the fluoroalkoxy group having a number of carbon atoms of 1 to 20, the aryl group having a number of carbon atoms of 6 to 20 and the aryloxy group having a number of carbon atoms of 6 to 20 include the same groups as described above.

It is preferable that $R^{14}$, $R^{15}$ and $R^{16}$ represent each independently a hydrogen atom, a fluorine atom, an alkyl group having a number of carbon atoms of 1 to 20, an alkoxy group having a number of carbon atoms of 1 to 20 or a fluoroalkoxy group having a number of carbon atoms of 1 to 20, it is more preferable that $R^{14}$, $R^{15}$ and $R^{16}$ represent each independently a hydrogen atom, a fluorine atom, an alkyl group having a number of carbon atoms of 1 to 6 or an alkoxy group having a number of carbon atoms of 1 to 6. It is preferable that any one of $R^{14}$, $R^{15}$ and $R^{16}$ represents a fluorine atom, an alkyl group having a number of carbon atoms of 1 to 6 or an alkoxy group having a number of carbon atoms of 1 to 6 and the remaining two represent a hydrogen atom, it is more preferable that $R^{14}$, $R^{15}$ and $R^{16}$ represent a hydrogen atom.

Here, in the formula (G), all of $R^{13}$ to $R^{17}$ do not simultaneously represent a hydrogen atom, and when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20. Further, $R^{14}$ and $R^{15}$ may be linked to form a ring (for example, a benzene ring) together with a carbon atom to which they are linked, and $R^{15}$ and $R^{16}$ may be linked to form a ring (for example, a benzene ring) together with a carbon atom to which they are linked.

The phosphine represented by the formula (G) includes a phosphine represented by the formula (G) in which $A^3$ and $A^4$ represent a cyclopentyl group, $R^{13}$ represents a hydrogen atom and $R^{17}$ represents an alkoxy group having a number of carbon atoms of 1 to 6, a phosphine represented by the formula (G) in which $A^3$ and $A^4$ represent a cyclopentyl group, $R^{13}$ represents a hydrogen atom and $R^{17}$ represents an alkyl group having a number of carbon atoms of 2 to 6, a phosphine represented by the formula (G) in which $A^3$ and $A^4$ represent a cyclopentyl group and $R^{13}$ and $R^{17}$ represent each independently an alkoxy group having a number of carbon atoms of 1 to 6, a phosphine represented by the formula (G) in which $A^3$ and $A^4$ represent a cyclopentyl group and $R^{13}$ and $R^{17}$ represent the same alkoxy group having a number of carbon atoms of 1 to 6, a phosphine represented by the formula (G) in which $A^3$ and $A^4$ represent a cyclopentyl group, any one of $R^{14}$, $R^{15}$ and $R^{16}$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (G) in which $A^3$ and $A^4$ represent a cyclopentyl group and all of $R^{14}$, $R^{15}$ and $R^{16}$ represent a hydrogen atom, a phosphine represented by the formula (G) in which $A^3$ and $A^4$ represent a cyclopentyl group, $R^{13}$ represents a hydrogen atom, $R^{17}$ represents an alkoxy group having a number of carbon atoms of 1 to 6, any one of $R^{14}$, $R^{15}$ and $R^{16}$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (G) in which $A^3$ and $A^4$ represent a cyclopentyl group, $R^{13}$ represents a hydrogen atom, $R^{17}$ represents an alkoxy group having a number of carbon atoms of 1 to 6 and all of $R^{14}$, $R^{15}$ and $R^{16}$ represent a hydrogen atom, a phosphine represented by the formula (G) in which $A^3$ and $A^4$ represent a cyclopentyl group, $R^{13}$ represents a hydrogen atom, $R^{17}$ represents an alkyl group having a number of carbon atoms of 2 to 6, any one of $R^{14}$, $R^{15}$ and $R^{16}$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (G) in which $A^3$ and $A^4$ represent a cyclopentyl group, $R^{13}$ represents a hydrogen atom, $R^{17}$ represents an alkyl group having a number of carbon atoms of 2 to 6 and all of $R^{14}$, $R^{15}$ and $R^{16}$ represent a hydrogen atom, a phosphine represented by the formula (G) in which $A^3$ and $A^4$ represent a cyclopentyl group, $R^{13}$ and $R^{17}$ represent each independently an alkoxy group having a number of carbon atoms of 1 to 6, any one of $R^{10}$, $R^{15}$ and $R^{16}$ represents a fluorine atom, an alkyl group having a number of carbon atoms of 1 to 6 or an alkoxy group having a number of carbon atoms of 1 to 6 and the remaining two represent a hydrogen atom, a phosphine represented by the formula (G) in which $A^3$ and $A^4$ represent a cyclopentyl group, $R^{13}$ and $R^{17}$ represent each independently an alkoxy group having a number of carbon atoms of 1 to 6 and all of $R^{14}$, $R^{15}$ and $R^{16}$ represent a hydrogen atom, a phosphine represented by the formula (G) in which $A^3$ and $A^4$ represent a cyclopentyl group, $R^{13}$ and $R^{17}$ represent the same alkoxy group having a number of carbon atoms of 1 to 6, any one of $R^{14}$, $R^{15}$ and $R^{16}$ represents a fluorine atom, an alkyl group having a number of carbon atoms of 1 to 6 or an alkoxy group having a number of carbon atoms of 1 to 6 and the remaining two represent a hydrogen atom and a phosphine represented by the formula (G) in which $A^3$ and $A^4$ represent a cyclopentyl group, $R^{13}$ and $R^{17}$ represent the same alkoxy group having a number of carbon atoms of 1 to 6 and all of $R^{14}$, $R^{15}$ and $R^{16}$ represent a hydrogen atom.

Specific examples of the phosphine represented by the formula (G) include dicyclopentyl(4-fluorophenyl)phosphine, dicyclopentyl(3-fluorophenyl)phosphine, dicyclopentyl(2-fluorophenyl)phosphine, dicyclopentyl(4-methylphenyl)phosphine, dicyclopentyl(3-methylphenyl)phosphine, dicyclopentyl(4-ethylphenyl)phosphine, dicyclopentyl(3-ethylphenyl)phosphine, dicyclopentyl(2-ethylphenyl)phosphine, dicyclopentyl(4-isopropylphenyl)phosphine, dicyclopentyl(3-isopropylphenyl)phosphine, dicyclopentyl(2-isopropylphenyl)phosphine, dicyclopentyl(4-tert-butylphenyl)phosphine, dicyclopentyl(3-tert-butylphenyl)phosphine, dicyclopentyl(4-methoxyphenyl)phosphine, dicyclopentyl(3-methoxyphenyl)phosphine, dicyclopentyl(2-methoxyphenyl)phosphine, dicyclopentyl(2,6-dimethoxyphenyl)phosphine, dicyclopentyl(4-ethoxyphenyl)phosphine, dicyclopentyl(3-ethoxyphenyl)phosphine, dicyclopentyl(2-ethoxyphenyl)phosphine, dicyclopentyl(4-trifluoromethoxyphenyl)phosphine, dicyclopentyl(3-trifluoromethoxyphenyl)phosphine, dicyclopentyl(2-trifluoromethoxyphenyl)phosphine, dicyclopentyl(4-pentafluoroethoxyphenyl)phosphine, dicyclopentyl(3- pentafluoroethoxyphenyl)phosphine, dicyclopentyl(2-pentafluoroethoxyphenyl)phosphine, dicyclopentyl([1,1'-biphenyl]-4-yl)phosphine, dicyclopentyl([1,1'-biphenyl]-3-yl)phosphine, dicyclopentyl(4-phenoxyphenyl)phosphine, dicyclopentyl(3-phenoxyphenyl)phosphine, dicyclopentyl(2-phenoxyphenyl)phosphine, dicyclopentyl(4-fluoro-2-methoxyphenyl)phosphine, dicyclopentyl(4-methoxy-2-methoxyphenyl)phosphine, dicyclopentyl(4-trifluoromethyl-2-methoxyphenyl)phosphine and dicyclopentyl(2-naphthyl)phosphine.

Phosphonium Salt Represented by the Formula (H)

The phosphonium salt represented by the formula (F) is preferably a phosphonium salt represented by the following formula (H).

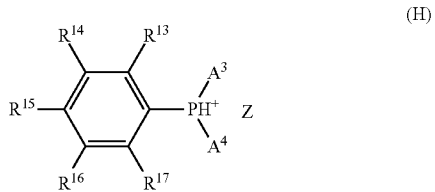

(H)

In the formula, $A^3$, $A^4$, $R^{13}$ to $R^{17}$ and Z represent the same meaning as described above.

Specific examples of the phosphonium salt represented by the formula (F) include dicyclopentyl(4-fluorophenyl)phosphonium tetrafluoroborate, dicyclopentyl(3-fluorophenyl)phosphonium tetrafluoroborate, dicyclopentyl(2-fluorophenyl)phosphonium tetrafluoroborate, dicyclopentyl(4-methylphenyl)phosphonium tetrafluoroborate, dicyclopentyl(3-methylphenyl)phosphonium tetrafluoroborate, dicyclopentyl(4-ethylphenyl)phosphonium tetrafluoroborate, dicyclopentyl(3-ethylphenyl)phosphonium tetrafluoroborate, dicyclopentyl(2-ethylphenyl)phosphonium tetrafluoroborate, dicyclopentyl(4-isopropylphenyl)phosphonium tetrafluoroborate, dicyclopentyl(3-isopropylphenyl)phosphonium tetrafluoroborate, dicyclopentyl(2-isopropylphenyl)phosphonium tetrafluoroborate, dicyclopentyl(4-tert-butylphenyl)phosphonium tetrafluoroborate, dicyclopentyl(3-tert-butylphenyl)phosphonium tetrafluoroborate, dicyclopentyl(4-methoxyphenyl)phosphonium tetrafluoroborate, dicyclopentyl(3-methoxyphenyl)phosphonium tetrafluoroborate, dicyclopentyl(2-methoxyphenyl)phosphonium tetrafluoroborate, dicyclopentyl(2,6-dimethoxyphenyl)phosphonium tetrafluoroborate, dicyclopentyl(4-ethoxyphenyl)phosphonium tetrafluoroborate, dicyclopentyl(3-ethoxyphenyl)phosphonium tetrafluoroborate, dicyclopentyl(2-ethoxyphenyl)phosphonium tetrafluoroborate, dicyclopentyl(4-trifluoromethoxyphenyl)phosphonium tetrafluoroborate, dicyclopentyl(3-trifluoromethoxyphenyl)phosphonium tetrafluoroborate, dicyclopentyl(2-trifluoromethoxyphenyl)phosphonium tetrafluoroborate, dicyclopentyl(4-pentafluoroethoxyphenyl)phosphonium tetrafluoroborate, dicyclopentyl(3-pentafluoroethoxyphenyl)phosphonium tetrafluoroborate, dicyclopentyl(2-pentafluoroethoxyphenyl)phosphonium tetrafluoroborate, dicyclopentyl([1,1'-biphenyl]-4-yl)phosphonium tetrafluoroborate, dicyclopentyl([1,1'-biphenyl]-3-yl)phosphonium tetrafluoroborate, dicyclopentyl(4-phenoxyphenyl)phosphonium tetrafluoroborate, dicyclopentyl(3-phenoxyphenyl)phosphonium tetrafluoroborate, dicyclopentyl(2-phenoxyphenyl)phosphonium tetrafluoroborate, dicyclopentyl(4-fluoro-2-methoxyphenyl)phosphonium tetrafluoroborate, dicyclopentyl(4-methoxy-2-methoxyphenyl)phosphonium tetrafluoroborate, dicyclopentyl(4-trifluoromethyl-2-methoxyphenyl)phosphonium tetrafluoroborate, and, dicyclopentyl(2-naphthyl)phosphonium tetrafluoroborate, dicyclopentyl(2-methoxyphenyl)phosphonium tetraphenyl borate, dicyclopentyl(2,6-dimethoxyphenyl)phosphonium tetraphenyl borate, dicyclopentyl(2-methoxyphenyl)phosphonium tetramesityl borate and dicyclopentyl(2,6-dimethoxyphenyl)phosphonium tetramesityl borate.

The at least one phosphine compound selected from the group consisting of a phosphine represented by the formula (C) and a phosphonium salt represented by the formula (F) is preferably a phosphine represented by the formula (C).

The use amount of the phosphine compound is usually in the range of 0.1 mol to 10 mol, preferably in the range of 0.5 mol to 5 mol with respect to 1 mol of a palladium compound.

The phosphine represented by the formula (C) can be synthesized according to known methods described in Journal of Molecular Catalysis A: Chemical 2003, 200, 81-94, and the like. Further, commercially available phosphines represented by the formula (C) can also be used.

The phosphonium salt represented by the formula (F) can be synthesized from the corresponding phosphine according to a known method described in Organic Letters 2001, Vol. 3, No. 26, 4295-4298.

The phosphine represented by the formula (G) or the phosphonium salt represented by the formula (H) can also be used, for example, as a ligand in a coupling reaction described in Metal-Catalyzed Cross-Coupling Reactions Second, Completely Revised and Enlarged Edition Volume 1,2 (de Meijere Armin, Diederich Francois ed., 2004, published by Wiley-VCH). Specific examples of the coupling reaction include the Stille coupling, the Heck coupling, the Hiyama coupling, the Sonogashira coupling, the Kumada coupling and the Buchwald-Hartwig coupling.

<Transition Metal Complex>

A transition metal complex can be produced by contacting a phosphine represented by the formula (G) and a group X transition metal complex. Here, "group X transition metal compound" includes, for example, a nickel compound, a palladium compound, a platinum compound and the like. Preferably, a palladium compound and the like are mentioned. Here, "palladium compound" includes, for example, palladium compounds described in the above-described section of explanation of <Palladium compound>, and the like.

The transition metal complex composed of a palladium compound and the above-described phosphine compound or phosphine represented by the formula (G) can be produced according to known methods described, for example, in Vol. 5 Jikken Kagaku Koza (The Chemical Society of Japan ed., published by Maruzen K. K.) 21 Organic transition metal complex•supermolecule complex, p. 308-327 (9.2 Organic palladium complex) and the like.

<Reaction Step>

The production method of the present invention comprises a step of mixing a compound represented by the formula (A) and a compound represented by the formula (B) in the presence of a base, a palladium compound, at least one phosphine compound selected from the group consisting of a phosphine represented by the formula (C) and a phosphonium salt represented by the formula (F) and an aprotic organic solvent, and an aromatic compound is generated by reacting a compound represented by the formula (A) and a compound represented by the formula (B). The mixing order of them is not particularly restricted, and for example, a palladium compound, the above-described phosphine compound, a base, a compound represented by the formula (A), a compound represented by the formula (B) and an aprotic organic solvent may be mixed simultaneously. It may also be permissible that a base, a compound represented by the formula (A), a compound represented by the formula (B) and an aprotic organic solvent are mixed, then, the resultant mixture, an aprotic organic solvent, a palladium compound and the above-described phosphine compound are mixed. Further, it may also be permissible that the above-described phosphine compound and a palladium compound are previously contacted to obtain a transition metal complex, then, a base, a compound represented by the formula (A), a compound represented by the formula (B) and an aprotic organic solvent are mixed to obtain a mixture, and this mixture is mixed with the above-described transition metal complex.

An aromatic compound represented by the following formula (H-1) is obtained by reacting a compound (A-1) and a compound (B-1).

$Ar_1$—$Ar_2$ (H-1)

An aromatic compound represented by the following formula (H-2) is obtained by reacting a compound (A-1) and a compound (B-2).

$Ar_1$—$Ar_2$—$Ar_1$ (H-2)

An aromatic compound represented by the following formula (H-3) is obtained by reacting a compound (A-2) and a compound (B-1).

$Ar_2$—$Ar_1$—$Ar_2$ (H-3)

An aromatic compound having a structural unit represented by the following formula (H-4) is obtained by reacting a compound (A-2) and a compound (B-2) (wherein, $Ar^1$ and $Ar^2$ represent the same meaning as described above).

$\left[ Ar_1 - Ar_2 \right]$ (H-4)

The reaction temperature is usually in the range of 0° C. to 180° C., preferably in the range of 30° C. to 100° C. The reaction time is usually in the range of 1 hour to 96 hours, preferably in the range of 3 hours to 48 hours.

After completion of the reaction, a reaction mixture containing an aromatic compound is obtained. The resultant aromatic compound can be isolated by a purification treatment such as chromatographic fractionation and the like. When the aromatic compound is an aromatic compound having a repeating unit represented by the above-described formula (G-4), for example, the targeted aromatic compound can be deposited by a method of mixing the reaction mixture and a poor solvent, and the aromatic compound can be isolated by a usual separation means such as filtration and the like. For removing impurities such as palladium and the like, the reaction mixture may be washed with an acidic solution such as hydrochloric acid and the like before isolation of the targeted aromatic compound.

EXAMPLES

The present invention will be illustrated further in detail by examples below.

When the resultant aromatic compound is an aromatic compound represented by the above-described formulae (H-1) to (H-3), the yield was obtained by purifying by silica gel column chromatography. When the resultant aromatic compound is an aromatic compound having a repeating unit represented by the above-described formula (H-4), analysis was performed by gel permeation chromatography (hereinafter, abbreviated as GPC) (analysis conditions are as described below), and the polystyrene-equivalent weight-average molecular weight (Mw) and the polystyrene-equivalent number-average molecular weight (Mn) were calculated from the analysis results.

<Analysis Condition of GPC>

GPC measurement apparatus: CTO-20A (column oven manufactured by Shimadzu Corp.), SPD-20A (detector manufactured by Shimadzu Corp.)

Column: PLgel 10 μm MIXED-B 300×7.5 mm (manufactured by Polymer Laboratories Ltd.)

Column temperature: 40° C.

Mobile phase: tetrahydrofuran

Flow rate: 2 mL/min

Detection: UV detection (wavelength: 228 nm)

Example 1

Under a nitrogen atmosphere, into a glass reaction vessel equipped with a cooling apparatus were added 5.99 mmol of a boronate composed of 9,9-di-n-octylfluorene-2,7-diboronic acid and pinacol, 6.00 mmol of bis(4-bromophenyl) [4-(methylpropyl)phenyl]amine, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(dicyclopentyl(2-methoxyphenyl)phosphine)dichloropalladium(II) and 12 ml of toluene. The resultant mixture was heated at a bath temperature of 100° C. while stirring and reacted for 4 hours, to obtain a reaction mixture containing an aromatic compound composed of the following repeating structural unit. The molecular weight of the resultant aromatic reaction mixture was analyzed by GPC, to find a molecular weight (Mw) of $3.9 \times 10^5$.

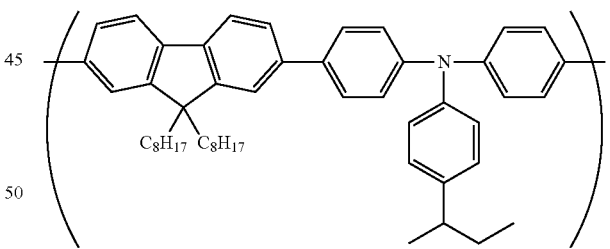

Example 2

The present example was carried out in the same manner as in Example 1 excepting that bis(dicyclopentyl(4-methoxyphenyl)phosphine)dichloropalladium(II) was used instead of bis(dicyclopentyl(2-methoxyphenyl)phosphine)dichloropalladium(II) in Example 1. The resultant aromatic compound had a molecular weight (Mw) of $3.1 \times 10^5$.

Example 3

The present example was carried out in the same manner as in Example 1 excepting that bis(dicyclopentyl(2-ethylphenyl)phosphine)dichloropalladium(II) was used instead of bis (dicyclopentyl(2-methoxyphenyl)phosphine)dichloropalladium(II) in Example 1. The resultant aromatic compound had a molecular weight (Mw) of $2.0 \times 10^5$.

The structural formulae of the phosphine compounds used in Examples 1 to 3 and the molecular weights (Mw) of the resultant aromatic compounds are shown in Table 1 described below.

TABLE 1

| Example | Structural formula of phosphine compound | Molecular weight (Mw) of aromatic compound |
|---|---|---|
| 1 | | $3.9 \times 10^5$ |
| 2 | | $3.1 \times 10^5$ |
| 3 | | $2.0 \times 10^5$ |

Example 4

Under a nitrogen atmosphere, into a glass reaction vessel equipped with a cooling apparatus were added 5.96 mmol of a boronate composed of 9,9-di-n-octylfluorene-2,7-diboronic acid and pinacol, 6.00 mmol of bis(4-bromophenyl) [4-(methylpropyl)phenyl]amine, 20 ml of a 20 wt % tetraethylammonium hydroxide aqueous solution and 110 mL of toluene at room temperature. The resultant mixture was heated at a bath temperature of 100° C. while stirring. To the mixture were added 3 µmol of bis(dicyclopentyl(2,6-dimethoxyphenyl)phosphine)dichloropalladium(II) and 12 ml of toluene. The resultant mixture was heated at a bath temperature of 100° C. while stirring and reacted for 4 hours, to obtain a reaction mixture containing an aromatic compound composed of the following repeating structural unit. The molecular weight of the resultant aromatic reaction mixture was analyzed by GPC, to find a molecular weight (Mw) of $3.1 \times 10^5$.

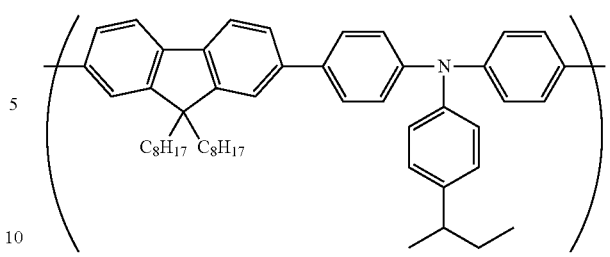

The structural formula of the phosphine compound used in Example 4 and the molecular weight (Mw) of the resultant aromatic compound are shown in Table 2 described below.

TABLE 2

| Example | Structural formula of phosphine compound | Molecular weight (Mw) of aromatic compound |
|---|---|---|
| 4 | | $3.1 \times 10^5$ |

Example 5

Under a nitrogen atmosphere, into a glass reaction vessel equipped with a cooling apparatus were added 5.97 mmol of a boronate composed of 9,9-di-n-octylfluorene-2,7-diboronic acid and pinacol, 6.00 mmol of bis(4-bromophenyl)[4-(methylpropyl)phenyl]amine, 20 ml of a 20 wt % tetraethylammonium hydroxide aqueous solution and 110 mL of toluene at room temperature. The resultant mixture was heated at a bath temperature of 100° C. while stirring. To the mixture were added 3 µmol of bis(dicyclopentyl(2,6-dimethoxyphenyl)phosphine)dichloropalladium(II) and 12 ml of toluene. The resultant mixture was heated at a bath temperature of 100° C. while stirring and reacted for 4 hours, to obtain a reaction mixture containing an aromatic compound composed of the following repeating structural unit. The molecular weight of the resultant aromatic reaction mixture was analyzed by GPC, to find a molecular weight (Mw) of $3.8 \times 10^5$.

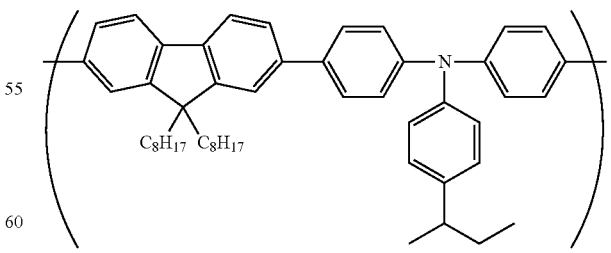

Example 6

The present example was carried out in the same manner as in Example 5 excepting that bis(dicyclopentyl(2-methoxyphenyl)phosphine)dichloropalladium(II) was used instead of bis(dicyclopentyl(2,6-dimethoxyphenyl)phosphine)dichloropalladium(II) in Example 5. The resultant aromatic compound had a molecular weight (Mw) of $2.2 \times 10^5$.

Example 7

The present example was carried out in the same manner as in Example 5 excepting that bis(dicyclopentyl(3-methoxyphenyl)phosphine)dichloropalladium(II) was used instead of bis(dicyclopentyl(2,6-dimethoxyphenyl)phosphine)dichloropalladium(II) in Example 5. The resultant aromatic compound had a molecular weight (Mw) of $1.9 \times 10^5$.

Example 8

The present example was carried out in the same manner as in Example 5 excepting that bis(dicyclopentyl(4-methylphenyl)phosphine)dichloropalladium(II) was used instead of bis(dicyclopentyl(2,6-dimethoxyphenyl)phosphine)dichloropalladium(II) in Example 5. The resultant aromatic compound had a molecular weight (Mw) of $1.9 \times 10^5$.

Example 9

The present example was carried out in the same manner as in Example 5 excepting that bis(dicyclopentyl([1,1'-biphenyl]-2-yl)phosphine)dichloropalladium(II) was used instead of bis(dicyclopentyl(2,6-dimethoxyphenyl)phosphine)dichloropalladium(II) in Example 5. The resultant aromatic compound had a molecular weight (Mw) of $2.0 \times 10^5$.

Example 10

The present example was carried out in the same manner as in Example 5 excepting that bis(dicyclopentyl(4-fluoro-2-methoxyphenyl)phosphine)dichloropalladium(II) was used instead of bis(dicyclopentyl(2,6-dimethoxyphenyl)phosphine)dichloropalladium(II) in Example 5. The resultant aromatic compound had a molecular weight (Mw) of $2.1 \times 10^5$.

The structural formulae of the phosphine compounds used in Examples 5 to 10 and the molecular weights (Mw) of the resultant aromatic compounds are shown in Table 3 described below.

TABLE 3

| Example | Structural formula of phosphine compound | Molecular weight (Mw) of aromatic compound |
| --- | --- | --- |
| 5 | [MeO, OMe substituted phenyl with P(cyclopentyl)₂] | $3.8 \times 10^5$ |
| 6 | [OMe substituted phenyl with P(cyclopentyl)₂] | $2.2 \times 10^5$ |
| 7 | [3-OMe substituted phenyl with P(cyclopentyl)₂] | $1.9 \times 10^5$ |
| 8 | [4-Me substituted phenyl with P(cyclopentyl)₂] | $1.9 \times 10^5$ |
| 9 | [2-Ph substituted phenyl with P(cyclopentyl)₂] | $2.0 \times 10^5$ |
| 10 | [4-F, 2-OMe substituted phenyl with P(cyclopentyl)₂] | $2.1 \times 10^5$ |

Example 11

The reaction was carried out in the same manner as in Example 5 excepting that 1.5 mol of tris(dibenzylideneacetone)dipalladium(0) and 6 µmol of dicyclopentyl(2-methoxyphenyl)phosphine were used instead of bis(dicyclopentyl(2,6-dimethoxyphenyl)phosphine)dichloropalladium(II) in Example 5, to obtain a mixture containing an aromatic compound. The resultant aromatic compound had a molecular weight (Mw) of $2.3 \times 10^5$.

Comparative Example 1

The reaction was carried out for 6 hours in the same manner as in Example 5 excepting that 1.5 µmol of tris(dibenzylideneacetone)dipalladium(0) and 6 µmol of tri-tert-butylphosphine tetrafluoroborate were used instead of bis(dicyclopentyl(2,6-dimethoxyphenyl)phosphine)dichloropalladium(II) in Example 5, to obtain a mixture containing an aromatic compound. The resultant aromatic compound had a molecular weight (Mw) of $2.8 \times 10^4$.

Example 12

The reaction was carried out for 5 hours in the same manner as in Example 5 excepting that 3 μmol of palladium acetate and 6 μmol of dicyclopentyl(2-methoxyphenyl)phosphine were used instead of bis(dicyclopentyl(2,6-dimethoxyphenyl)phosphine)dichloropalladium(II) in Example 5, to obtain a mixture containing an aromatic compound. The resultant aromatic compound had a molecular weight (Mw) of $2.1 \times 10^5$.

Comparative Example 2

The reaction was carried out for 6 hours in the same manner as in Example 5 excepting that 1.5 μmol of tris(dibenzylideneacetone)dipalladium(0) and 6 μmol of 2-dicyclohexylphosphino-2',6'-dimethoxybiphenyl were used instead of bis(dicyclopentyl(2,6-dimethoxyphenyl)phosphine)dichloropalladium(II) in Example 5, to obtain a mixture containing an aromatic compound. The resultant aromatic compound had a molecular weight (Mw) of $1.2 \times 10^4$.

The structural formulae of the phosphine compounds used in Examples 11 to 12 and Comparative Examples 1 and 2 and the molecular weights (Mw) of the resultant aromatic compounds are shown in Table 4 described below.

TABLE 4

| Example | Palladium compound | Structural formula of phosphine compound | Molecular weight (Mw) of aromatic compound |
|---|---|---|---|
| 11 | Pd$_2$(dba)$_3$ | (structure: P with two cyclopentyl groups and 2-methoxyphenyl) | $2.3 \times 10^5$ |
| Comparative Example 1 | Pd$_2$(dba)$_3$ | (structure: PH$^+$ BF$_4^-$ with three tert-butyl groups) | $2.8 \times 10^5$ |
| 12 | Pd(OAc)$_2$ | (structure: P with two cyclopentyl groups and 2-methoxyphenyl) | $2.1 \times 10^5$ |

TABLE 4-continued

| Example | Palladium compound | Structural formula of phosphine compound | Molecular weight (Mw) of aromatic compound |
|---|---|---|---|
| Comparative Example 2 | Pd(OAc)$_2$ | (structure shown below) | $1.2 \times 10^5$ |

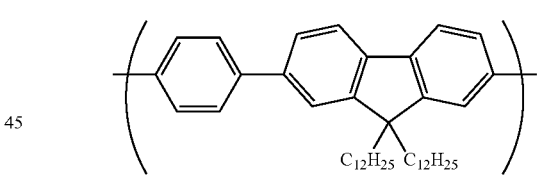

Example 13

Under a nitrogen atmosphere, into a glass reaction vessel equipped with a cooling apparatus were added 5.97 mmol of a boronate composed of benzene-1,4-diboronic acid and pinacol, 6.00 mmol of 2,7-dibromo-9,9-di-n-dodecylfluorene, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(dicyclopentyl(2,6-dimethoxyphenyl)phosphine)dichloropalladium(II) and 12 ml of toluene. The resultant mixture was reacted for 7 hours at a bath temperature of 100° C. while stirring, to obtain a reaction mixture containing an aromatic compound composed of the following repeating structural unit.

The molecular weight of the resultant aromatic compound was analyzed by GPC, to find a molecular weight (Mw) of $3.1 \times 10^5$.

(Structural formula showing repeating unit of phenylene-fluorene with C$_{12}$H$_{25}$ C$_{12}$H$_{25}$ substituents)

Example 14

Under a nitrogen atmosphere, into a glass reaction vessel equipped with a cooling apparatus were added 6.00 mmol of a boronate composed of benzene-1,4-diboronic acid and pinacol, 4.50 mmol of 2,7-dibromo-9,9-di-n-octylfluorene, 1.50 mmol of 4,7-dibromo-2,1,3-benzothiadiazole, 20 ml of a 20 wt % tetraethylammonium hydroxide aqueous solution and 110 mL of toluene at room temperature. The resultant mixture was heated at a bath temperature of 100° C. while stirring. To the mixture were added 3 μmol of bis(dicyclopentyl(2,6-dimethoxyphenyl)phosphine)dichloropalladium(II) and 12 ml of toluene. The resultant mixture was reacted for 7 hours at a bath temperature of 100° C. while stirring, to obtain a reaction mixture containing an aromatic compound composed of the following repeating structural unit. The molecular weight of the resultant aromatic compound was analyzed by GPC, to find a molecular weight (Mw) of $2.8 \times 10^5$.

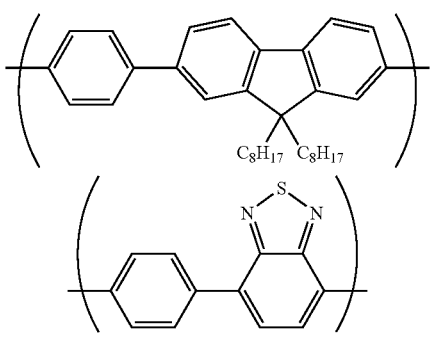

Example 15

Under a nitrogen atmosphere, into a glass reaction vessel equipped with a cooling apparatus were added 6.0 mmol of a boronate composed of 9,9-di-n-octylfluorene-2,7-diboronic acid and ethylene glycol, 6.0 mmol of bis(4-bromophenyl)[4-(methylpropyl)phenyl]amine, 1.2 mmol of Aliquat (registered trademark) 336 (manufactured by Sigma-Aldrich), 12 ml of a sodium carbonate aqueous solution having a concentration of 3 mol/L and 110 mL of toluene at room temperature. The resultant mixture was heated at a bath temperature of 100° C. while stirring. To the mixture were added 3 µmol of bis(dicyclopentyl(2-methoxyphenyl)phosphine)dichloropalladium(II) and 12 ml of toluene. The resultant mixture was reacted for 6 hours at a bath temperature of 100° C. while stirring, to obtain a reaction mixture containing an aromatic compound composed of the following repeating structural unit. The molecular weight of the resultant aromatic compound was analyzed by GPC, to find a molecular weight (Mw) of $2.0 \times 10^5$.

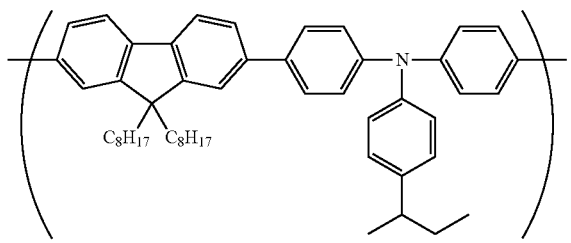

Example 16

Under a nitrogen atmosphere, into a reaction vessel equipped with a dropping funnel were added 0.91 g of 2-bromoanisole and 20 mL of tetrahydrofuran. The resultant solution was cooled down to −78° C., then, 3.4 ml of n-butyllithium (1.62 M/hexane solution) was dropped. The resultant mixture was stirred at the same temperature for 2 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, to obtain 1.73 g of a mixture in the form of viscous liquid containing dicyclopentyl(2-methoxyphenyl)phosphine.

Under a nitrogen atmosphere, into a reaction vessel were added the above-described mixture containing dicyclopentyl(2-methoxyphenyl)phosphine, 0.50 g of dichlorobis(acetonitrile)palladium(II) and 30 mL of ethanol. The resultant mixture was stirred at room temperature for 16 hours. A solid deposited in the resultant reaction mixture was isolated by filtration, and washed with 12 ml of ethanol three times. The resultant solid was dried under reduced pressure at 50° C. for 3 hours, to obtain 1.24 g of bis(dicyclopentyl(2-methoxyphenyl)phosphine)dichloropalladium(II) in the form of pale yellow solid.

$^1$H-NMR (δ: ppm, CDCl$_3$ solvent, TMS basis)
7.5 (m, 1H), 7.4 (m, 1H), 7.0 (m, 1H), 6.9 (m, 1H), 4.0 (s, 3H), 2.8 (quin, 2H), 2.1 (m, 4H), 2.0 (m, 4H), 1.6 (m, 8H)
$^{31}$P-NMR (δ: ppm, CDCl$_3$ solvent)
22.7

Example 17

Under a nitrogen atmosphere, into a reaction vessel equipped with a dropping funnel were added 0.91 g of 4-bromoanisole and 20 mL of tetrahydrofuran. The resultant solution was cooled down to −78° C., then, 3.0 mL of n-butyllithium (1.62 M/hexane solution) was dropped. The resultant mixture was stirred at the same temperature for 2 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, to obtain 1.58 g of a mixture in the form of viscous liquid containing dicyclopentyl(4-methoxyphenyl)phosphine.

Under a nitrogen atmosphere, into a reaction vessel were added the above-described mixture containing dicyclopentyl(4-methoxyphenyl)phosphine, 0.50 g of dichlorobis(acetonitrile)palladium(II) and 30 mL of ethanol. The resultant mixture was stirred for 14 hours at room temperature. A solid deposited in the resultant reaction mixture was isolated by filtration, and washed with 12 ml of ethanol three times. The resultant solid was dried under reduced pressure at 50° C. for 3 hours, to obtain 0.92 g of bis(dicyclopentyl(4-methoxyphenyl)phosphine)dichloropalladium(II) in the form of pale yellow solid.

$^1$H-NMR (δ: ppm, CDCl$_3$ solvent, TMS basis)
7.6 (m, 2H), 6.9 (m, 2H), 3.8 (s, 3H), 2.8 (quin, 2H), 2.1 (m, 2H), 1.9 (m, 6H), 1.6 (m, 8H)
$^{31}$P-NMR (δ: ppm, CDCl$_3$ solvent)
27.0

Example 18

Under a nitrogen atmosphere, into a reaction vessel equipped with a dropping funnel were added 1.06 g of 2-bromo-1,3-dimethoxybenzene and 20 mL of tetrahydrofuran. The resultant solution was cooled down to −78° C., then, 3.0 mL of n-butyllithium (1.62 M/hexane solution) was dropped. The resultant mixture was stirred at the same temperature for 3 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, to obtain 2.06 g of a mixture in the form of viscous liquid containing dicyclopentyl(2,6-dimethoxyphenyl)phosphine.

Under a nitrogen atmosphere, into a reaction vessel were added the above-described mixture containing dicyclopentyl(2,6-dimethoxyphenyl)phosphine, 0.50 g of dichlorobis(acetonitrile)palladium(II) and 30 mL of ethanol. The resultant mixture was stirred at room temperature for 16 hours. A solid deposited in the resultant reaction mixture was isolated by filtration, and washed with 12 ml of ethanol three times. The resultant solid was dried under reduced pressure at 50° C. for 3 hours, to obtain 0.82 g of bis(dicyclopentyl(2,6-dimethoxyphenyl)phosphine)dichloropalladium(II) in the form of yellow solid.

$^1$H-NMR (δ: ppm, CDCl$_3$ solvent, TMS basis)
7.3 (t, 1H), 6.6 (dt, 2H), 3.9 (s, 6H), 3.0 (quin, 2H), 1.8-2.0 (m, 8H), 1.6 (m, 8H)
$^{31}$P-NMR (δ: ppm, CDCl$_3$ solvent)
21.2

Example 19

Under a nitrogen atmosphere, into a reaction vessel equipped with a dropping funnel were added 0.90 g of 1-bromo-2-ethylbenzene and 20 mL of tetrahydrofuran. The resultant solution was cooled down to −78° C., then, 3.0 mL of n-butyllithium (1.62 M/hexane solution) was dropped. The resultant mixture was stirred at the same temperature for 3 hours, then, a solution obtained by dissolving 1.00 g of chlorodicyclopentylphosphine in 13 ml of tetrahydrofuran was dropped at −78° C. The resultant mixture was stirred at room temperature for 5 hours. The resultant reaction mixture was concentrated, to obtain 1.71 g of a mixture in the form of viscous liquid containing dicyclopentyl(2-ethylphenyl)phosphine.

Under a nitrogen atmosphere, into a reaction vessel were added the above-described mixture containing dicyclopentyl(2-ethylphenyl)phosphine, 0.50 g of dichlorobis(acetonitrile)palladium(II) and 30 mL of ethanol. The resultant mixture was stirred at room temperature for 16 hours. A solid deposited in the resultant reaction mixture was isolated by filtration, and washed with 12 ml of ethanol three times. The resultant solid was dried under reduced pressure at 50° C. for 3 hours, to obtain 0.85 g of bis(dicyclopentyl(2-ethylphenyl)phosphine)dichloropalladium(II) in the form of yellow solid.

$^1$H-NMR (δ: ppm, CDCl$_3$ solvent, TMS basis)
7.4 (m, 3H), 7.2 (m, 1H), 3.7 (q, 2H), 2.8 (quin, 2H), 2.1 (m, 2H), 1.6-1.9 (m, 14H), 1.4 (t, 3H)
$^{31}$P-NMR (δ: ppm, CDCl$_3$ solvent)
18.4

Example 20

Under a nitrogen atmosphere, into a reaction vessel equipped with a dropping funnel were added 1.14 g of 2-bromobiphenyl and 20 mL of tetrahydrofuran. The resultant solution was cooled down to −78° C., then, 3.0 mL of n-butyllithium (1.62 M/hexane solution) was dropped. The resultant mixture was stirred at the same temperature for 2 hours, then, a solution obtained by dissolving 1.00 g of chlorodicyclopentylphosphine in 13 ml of tetrahydrofuran was dropped at −78° C. The resultant mixture was stirred at room temperature for 4 hours. The resultant reaction mixture was concentrated, to obtain 2.06 g of a mixture in the form of viscous liquid containing dicyclopentyl([1,1'-biphenyl]-2-yl)phosphine.

Under a nitrogen atmosphere, into a reaction vessel were added the above-described mixture containing dicyclopentyl([1,1'-biphenyl]-2-yl)phosphine, 0.45 g of dichlorobis(acetonitrile)palladium(II) and 45 mL of ethanol. The resultant mixture was stirred at room temperature for 19 hours. A solid deposited in the resultant reaction mixture was isolated by filtration, and washed with 12 ml of ethanol three times. The resultant solid was dried under reduced pressure at 50° C. for 3 hours, to obtain 1.22 g of bis(dicyclopentyl([1,1'-biphenyl]-2-yl)phosphine)dichloropalladium(II) in the form of yellow solid.

$^1$H-NMR (δ: ppm, CDCl$_3$ solvent, TMS basis)
8.0 (m, 1H), 7.7 (m, 2H), 7.4 (m, 5H), 7.2 (m, 1H), 2.3 (quin, 2H), 1.3-2.0 (m, 16H)
$^{31}$P-NMR (δ: ppm, CDCl$_3$ solvent)
32.7

Example 21

Under a nitrogen atmosphere, into a reaction vessel equipped with a dropping funnel were added 0.84 g of 4-bromotoluene and 20 mL of tetrahydrofuran. The resultant solution was cooled down to −78° C., then, 3.0 mL of n-butyllithium (1.62 M/hexane solution) was dropped. The resultant mixture was stirred at the same temperature for 2 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, to obtain 1.61 g of a mixture in the form of viscous liquid containing dicyclopentyl(4-methylphenyl)phosphine.

Under a nitrogen atmosphere, into a reaction vessel were added the above-described mixture containing dicyclopentyl(4-methylphenyl)phosphine, 0.45 g of dichlorobis(acetonitrile)palladium(II) and 45 mL of ethanol. The resultant mixture was stirred at room temperature for 17 hours. A solid deposited in the resultant reaction mixture was isolated by filtration, and washed with 12 ml of ethanol three times. The resultant solid was dried under reduced pressure at 50° C. for 3 hours, to obtain 1.07 g of bis(dicyclopentyl(4-methylphenyl)phosphine)dichloropalladium(II) in the form of yellow solid.

$^1$H-NMR (δ: ppm, CDCl$_3$ solvent, TMS basis)
7.6 (m, 2H), 7.2 (m, 2H), 7.4 (m, 5H), 2.8 (quin, 2H), 2.4 (s, 3H), 1.5-2.1 (m, 16H)
$^{31}$P-NMR (δ: ppm, CDCl$_3$ solvent)
28.0

Example 22

Under a nitrogen atmosphere, into a reaction vessel equipped with a dropping funnel were added 0.91 g of 3-bromoanisole and 20 mL of tetrahydrofuran. The resultant solution was cooled down to −78° C., then, 3.0 mL of n-butyllithium (1.62 M/hexane solution) was dropped. The resultant mixture was stirred at the same temperature for 2 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, to obtain 1.68 g of a mixture in the form of viscous liquid containing dicyclopentyl(3-methoxyphenyl)phosphine.

Under a nitrogen atmosphere, into a reaction vessel were added the above-described mixture containing dicyclopentyl(3-methoxyphenyl)phosphine, 0.50 g of dichlorobis(acetonitrile)palladium(II) and 30 mL of ethanol. The resultant mixture was stirred at room temperature for 14 hours. A solid deposited in the resultant reaction mixture was isolated by filtration, and washed with 12 ml of ethanol three times. The resultant solid was dried under reduced pressure at 50° C. for 3 hours, to obtain 1.27 g of bis(dicyclopentyl(3-methoxyphenyl)phosphine)dichloropalladium(II) in the form of pale yellow solid.

$^1$H-NMR (δ: ppm, CDCl$_3$ solvent, TMS basis)
7.3 (m, 3H), 7.0 (m, 1H), 3.8 (s, 3H), 2.8 (quin, 2H), 2.1 (m, 2H), 2.0 (m, 2H), 1.8 (m, 4H), 1.6 (m, 8H)
$^{31}$P-NMR (δ: ppm, CDCl$_3$ solvent)
30.1

Example 23

Under a nitrogen atmosphere, into a reaction vessel equipped with a dropping funnel were added 1.00 g of 2-bromo-5-fluoroanisole and 20 mL of tetrahydrofuran. The resultant solution was cooled down to −78° C., then, 3.0 mL of n-butyllithium (1.62 M/hexane solution) was dropped. The resultant mixture was stirred at the same temperature for 3 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, to obtain 1.75 g of a mixture in the form of viscous liquid containing dicyclopentyl(4-fluoro-2-methoxyphenyl)phosphine.

Under a nitrogen atmosphere, into a reaction vessel were added the above-described mixture containing dicyclopentyl(4-fluoro-2-methoxyphenyl)phosphine, 0.50 g of dichlorobis(acetonitrile)palladium(II) and 30 mL of ethanol. The resultant mixture was stirred at room temperature for 18 hours. A solid deposited in the resultant reaction mixture was isolated by filtration, and washed with 12 ml of ethanol three times. The resultant solid was dried under reduced pressure at 50° C. for 3 hours, to obtain 0.55 g of bis(dicyclopentyl(4-fluoro-2-methoxyphenyl)phosphine)dichloropalladium(II) in the form of pale yellow solid.

$^1$H-NMR (δ: ppm, CDCl$_3$ solvent, TMS basis)
7.5 (m, 1H), 6.7 (m, 2H), 3.9 (s, 3H), 2.8 (quin, 2H), 2.1 (m, 2H), 2.0 (m, 2H), 1.5-2.1 (m, 16H)
$^{31}$P-NMR (δ: ppm, CDCl$_3$ solvent)
22.6

Example 24

Under a nitrogen atmosphere, into a reaction vessel equipped with a dropping funnel were added 0.91 g of 2-bromoanisole and 20 mL of tetrahydrofuran. The resultant solution was cooled down to −78° C., then, 3.4 ml of n-butyllithium (1.62 M/hexane solution) was dropped. The resultant mixture was stirred at the same temperature for 2 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, and purified by silica gel column chromatography, to obtain 1.19 g of dicyclopentyl(2-methoxyphenyl)phosphine in the form of viscous liquid.

$^1$H-NMR (δ: ppm, CDCl$_3$ solvent, TMS basis)
7.4 (m, 1H), 7.3 (m, 1H), 7.0 (m, 1H), 6.9 (m, 1H), 3.9 (s, 3H), 2.3 (m, 2H), 1.9 (m, 2H), 1.7 (m, 2H), 1.4-1.6 (m, 10H), 1.2 (m, 2H)
$^{31}$P-NMR (δ: ppm, CDCl$_3$ solvent)
−7.8

Example 25

Under a nitrogen atmosphere, into a reaction vessel equipped with a dropping funnel were added 1.06 g of 2-bromo-1,3-dimethoxybenzene and 20 mL of tetrahydrofuran. The resultant solution was cooled down to −78° C., then, 3.0 mL of n-butyllithium (1.62 M/hexane solution) was dropped. The resultant mixture was stirred at the same temperature for 3 hours, then, a solution obtained by dissolving 1.00 g of chlorodicyclopentylphosphine in 13 ml of tetrahydrofuran was dropped at −78° C. The resultant mixture was stirred at room temperature for 3 hours. The resultant reaction mixture was concentrated, and purified by silica gel column chromatography, to obtain 0.37 g of a mixture in the form of viscous liquid containing dicyclopentyl(2,6-dimethoxyphenyl)phosphine.

$^1$H-NMR (δ: ppm, CDCl$_3$ solvent, TMS basis)
7.2 (m, 1H), 6.5 (m, 2H), 3.8 (s, 6H), 2.7 (m, 2H), 1.9 (m, 2H), 1.7 (m, 2H), 1.4-1.6 (m, 10H), 1.2 (m, 2H)
$^{31}$P-NMR (δ: ppm, CDCl$_3$ solvent)
−12.5

Examples 26 to 29

Into a glass reaction vessel equipped with a cooling apparatus were added 0.0075 mmol of bis(dicyclopentyl(2-methoxyphenyl)phosphine)dichloropalladium(II), 1.5 mmol of a compound (1) shown in Table 5, 1.65 mmol of a compound (2) shown in Table 5, 3.0 mmol of potassium phosphate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution containing the targeted compound (3). The yield of the compound (3) was determined by concentrating the resultant solution, and purifying the resultant coarse product by silica gel column chromatography. The results are shown in Table 5.

Examples 30 to 32

Into a glass reaction vessel equipped with a cooling apparatus were added 0.0075 mmol of bis(dicyclopentyl(2-methoxyphenyl)phosphine)dichloropalladium(II), 0.3 mmol of trioctylmethylammonium chloride, 1.5 mmol of a compound (1) shown in Table 6, 1.65 mmol of a compound (2) shown in Table 6, 3.0 mmol of sodium carbonate, 6 mL of toluene and 1.5 mL of water. The resultant mixture was stirred with heating at 100° C. for 3 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution containing the targeted compound (3). The yield of the compound (3) was determined by concentrating the resultant solution, and purifying the resultant coarse product by silica gel column chromatography. The results are shown in Table 6.

TABLE 5

| Example | compound (1) |
| --- | --- |
| 26 | ![2-bromo-4-methyltoluene structure]—Br |
| 27 | ![3-bromotoluene structure]—Br |
| 28 | ![2-bromothiophene structure]—Br |

TABLE 5-continued

| | |
|---|---|
| 29 | [structure: 2-chloroquinoline] |

| Example | compound (2) |
|---|---|
| 26 | (HO)₂B–[2-methylphenyl] |
| 27 | (HO)₂B–[thiophen-3-yl] |
| 28 | (HO)₂B–[4-methylphenyl] |
| 29 | (HO)₂B–[4-methylphenyl] |

| Example | compound (3) |
|---|---|
| 26 | [2,2'-dimethyl-4-methylbiphenyl] |
| 27 | [3-methylphenyl-3-thienyl] |
| 28 | [2-(4-methylphenyl)thiophene] |
| 29 | [2-(4-methylphenyl)quinoline] |

| | Yield (%) |
|---|---|
| 26 | 92 |
| 27 | 94 |
| 28 | 76 |
| 29 | 96 |

TABLE 6

| Example | compound (1) |
|---|---|
| 30 | [ethyl 4-chlorobenzoate] |
| 31 | [2-bromo-1,3-dimethoxybenzene] |
| 32 | [2-bromo-1,3-dimethylbenzene] |

| | compound (2) |
|---|---|
| | (HO)₂B–[4-methylphenyl] |
| | (HO)₂B–[4-methylphenyl] |
| | (HO)₂B–[2-methylphenyl] |

| Example | compound (3) |
|---|---|
| 30 | [ethyl 4'-methylbiphenyl-4-carboxylate] |
| 31 | [2,6-dimethoxy-4'-methylbiphenyl] |
| 32 | [2,2',6-trimethylbiphenyl] |

| Example | Yield (%) |
|---|---|
| 30 | 87 |
| 31 | 99 |
| 32 | 73 |

Example 33

Into a glass reaction vessel equipped with a cooling apparatus were added 0.015 mmol of bis(dicyclopentyl(2-methoxyphenyl)phosphine)dichloropalladium(II), 1.5 mmol of 3-bromopyridine, 2.25 mmol of 3-thiopheneboronic acid, 3.0 mmol of potassium phosphate and 4 mL of n-butanol. The resultant mixture was stirred with heating at 100° C. for 4 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution. This solution was concentrated, and purified by silica gel column chromatography, to obtain 3-(3-thienyl)-pyridine with a yield of 92%.

Example 34

Into a glass reaction vessel equipped with a cooling apparatus were added 0.015 mmol of bis(dicyclopentyl(2-methoxyphenyl)phosphine)dichloropalladium(II), 1.5 mmol of 3-bromothiophene, 2.25 mmol of 3-thiopheneboronic acid, 3.0 mmol of potassium phosphate and 4 mL of n-butanol. The resultant mixture was stirred with heating at 100° C. for 4 hours. The resultant reaction mixture was cooled down to room temperature, 20 mL of water was added, and the mixture was extracted with 20 mL of diethyl ether twice. The resultant organic layers were mixed, and dried over anhydrous magnesium sulfate, then, filtrated, to obtain a solution. This solution was concentrated, and purified by silica gel column chromatography, to obtain 3-(3-thienyl)-thiophene with a yield of 98%.

INDUSTRIAL APPLICABILITY

According to the present invention, an aromatic compound can be produced.

The invention claimed is:

1. A method of producing an aromatic compound, comprising a step of mixing a compound represented by the formula (A):

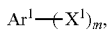
(A)

wherein, $X^1$ represents a group represented by the formula (1), (2), (3), (4), (5) or (6):

(1)

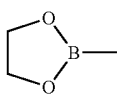
(2)

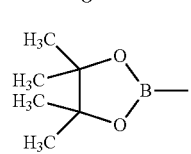
(3)

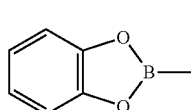
(4)

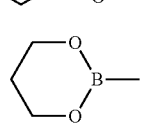
(5)

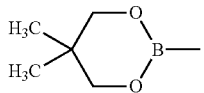
(6)

$Ar^1$ represents a monovalent or divalent aromatic hydrocarbon group having a number of carbon atoms of 6 to 36, and m represents 1 or 2, a carbon atom contained in the aromatic hydrocarbon group may be substituted with a hetero atom or a carbonyl group, and a hydrogen atom contained in the aromatic hydrocarbon group may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group, and a compound represented by the formula (B):

(B)

wherein, $X^2$ represents a chlorine atom, a bromine atom, an iodine atom, an alkylsulfonyloxy group, a fluorine-substituted alkylsulfonyloxy group or an arylsulfonyloxy group, $Ar^2$ represents a monovalent or divalent aromatic hydrocarbon group having a number of carbon atoms of 6 to 36, and n represents 1 or 2, a carbon atom contained in the aromatic hydrocarbon group may be substituted with a hetero atom or a carbonyl group, and a hydrogen atom contained in the aromatic hydrocarbon group may be substituted with a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocyclic group which may have a substituent, an amino group which may have a substituent, a silyl group which may have a substituent, an acyl group, a group having a carbon atom-nitrogen atom double bond as a partial structure, an acid imide group, an alkoxycarbonyl group, a cycloalkoxycarbonyl group, an aryloxycarbonyl group, a carboxyl group, a cyano group or a nitro group, in the presence of at least one phosphine compound selected from the group consisting of a phosphine represented by the formula (C):

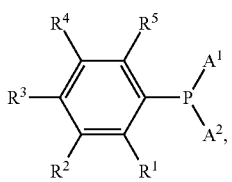
(C)

wherein, $A^1$ and $A^2$ represent each independently a cyclopentyl group which may have a substituent, $R^1$ and $R^5$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20, an aryloxy group having a number of carbon atoms of 6 to 20, a group represented by the formula (D):

(D)

wherein, $R^6$ represents a hydrogen atom, an alkyl group having a number of carbon atoms of 1 to 20 or a cycloalkyl group having a number of carbon atoms of 3 to 20, $R^7$ and $R^8$ represent each independently an alkyl group having a number of carbon atoms of 1 to 20 or a cycloalkyl group having a number of carbon atoms of 3 to 20, and $R^7$ and $R^8$ may be linked to form a ring, or a group represented by the formula (E):

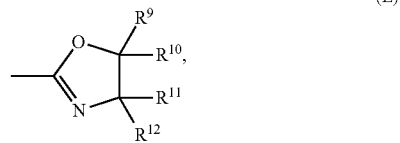

(E)

wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20, $R^2$, $R^3$ and $R^4$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20, here, all of $R^1$ to $R^5$ do not simultaneously represent a hydrogen atom, and, when at least one of $R^1$ to $R^5$ is a fluoroalkyl group having a number of carbon atoms of 1 to 20, at least one of the remaining $R^1$ to $R^5$ is not a hydrogen atom or a fluoroalkyl group having a number of carbon atoms of 1 to 20, further, $R^2$ and $R^3$ may be linked to form a ring together with a carbon atom to which they are linked, and $R^3$ and $R^4$ may be linked to form a ring together with a carbon atom to which they are linked, and a phosphonium salt represented by the formula (F):

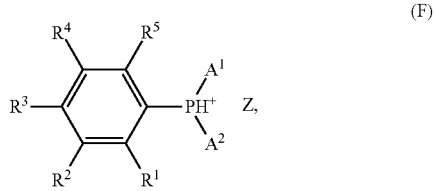

(F)

wherein, $A^1$, $A^2$, $R^1$ to $R^5$ represent the same meaning as described above, and Z represents an anion;

a base, a palladium compound and an aprotic organic solvent.

2. The production method of an aromatic compound according to claim 1, wherein $A^1$ and $A^2$ are a cyclopentyl group which may have an alkyl group having a number of carbon atoms of 1 to 20 or an aryl group having a number of carbon atoms of 6 to 20 as a substituent.

3. The production method of an aromatic compound according to claim 1, wherein $A^1$ and $A^2$ are a cyclopentyl group.

4. The production method of an aromatic compound according to claim 1, wherein at least one selected from $R^1$ and $R^5$ is an alkoxy group having a number of carbon atoms of 1 to 20.

5. The production method of an aromatic compound according to claim 1, wherein $R^2$, $R^3$ and $R^4$ are a hydrogen atom.

6. The production method of an aromatic compound according to claim 1, wherein the phosphine compound is at least one selected from the group consisting of a phosphine represented by the formula (G):

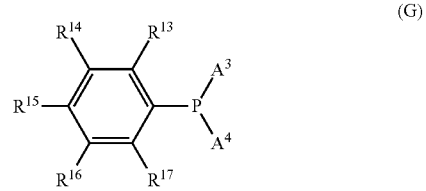

(G)

wherein, $A^3$ and $A^4$ represent each independently a cyclopentyl group which may have a substituent, $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the formula (E):

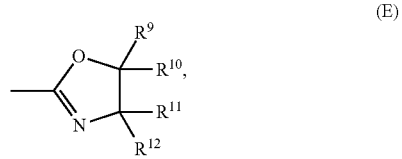

(E)

wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20, $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20, here, all of $R^{13}$ to $R^{17}$ do not simultaneously represent a hydrogen atom, and, when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20, further, $R^{14}$ and $R^{15}$ may be linked to form a ring together with a carbon atom to which they are linked, and $R^{15}$ and $R^{16}$ may be linked to form a ring together with a carbon atom to which they are linked, and a phosphonium salt represented by the formula (H):

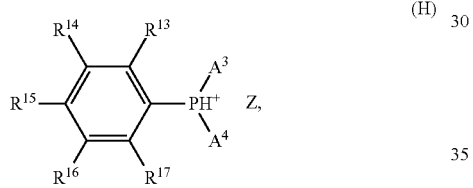

(H)

wherein, $A^3$, $A^4$, $R^{13}$ to $R^{17}$ and Z represent the same meaning as described above.

7. The production method of an aromatic compound according to claim 1, wherein the aprotic organic solvent is at least one selected from the group consisting of ether solvents, aromatic hydrocarbon solvents and aliphatic hydrocarbon solvents.

8. The production method of an aromatic compound according to claim 1, wherein the palladium compound is a palladium(0) complex or a palladium(II) complex.

9. A phosphine represented by the formula (G):

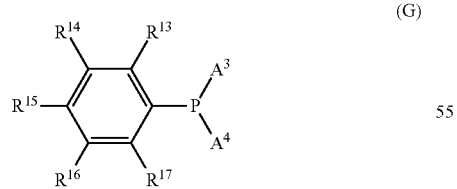

(G)

wherein, $A^3$ and $A^4$ represent each independently a cyclopentyl group which may have a substituent, $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the formula (E):

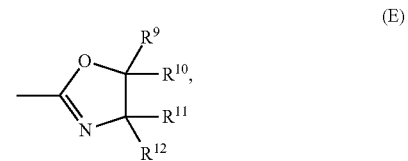

(E)

wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20, $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20, here, all of $R^{13}$ to $R^{17}$ do not simultaneously represent a hydrogen atom, and, when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20, further, $R^{14}$ and $R^{15}$ may be linked to form a ring together with a carbon atom to which they are linked, and $R^{15}$ and $R^{16}$ may be linked to form a ring together with a carbon atom to which they are linked.

10. The phosphine according to claim 9, wherein $A^3$ and $A^4$ are a cyclopentyl group which may have an alkyl group having a number of carbon atoms of 1 to 20 or an aryl group having a number of carbon atoms of 6 to 20 as a substituent.

11. The phosphine according to claim 9, wherein $A^3$ and $A^4$ are a cyclopentyl group.

12. The phosphine according to claim 9, wherein at least one selected from $R^{13}$ and $R^{17}$ is an alkoxy group having a number of carbon atoms of 1 to 20.

13. The phosphine according to claim 9, wherein $R^{14}$, $R^{15}$ and $R^{16}$ are a hydrogen atom.

14. A phosphonium salt represented by the formula (H):

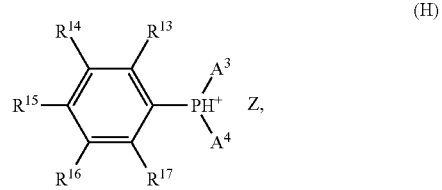

(H)

wherein, $A^3$ and $A^4$ represent each independently a cyclopentyl group which may have a substituent, $R^{13}$ and $R^{17}$ represent each independently a hydrogen atom, a fluorine atom, an alkyl group having a number of carbon atoms of 2 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryloxy group having a number of carbon atoms of 6 to 20 or a group represented by the formula (E):

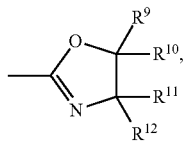
(E)

wherein, $R^9$, $R^{10}$, $R^{11}$ and $R^{12}$ represent each independently a hydrogen atom, an alkyl group having a number of carbon atoms of 1 to 20, a cycloalkyl group having a number of carbon atoms of 3 to 20 or an aryl group having a number of carbon atoms of 6 to 20, $R^{14}$, $R^{15}$ and $R^{16}$ represent each independently a hydrogen atom, a fluorine atom, an alkyl group having a number of carbon atoms of 1 to 20, a cycloalkyl group having a number of carbon atoms of 3 to 20, a fluoroalkyl group having a number of carbon atoms of 1 to 20, an alkoxy group having a number of carbon atoms of 1 to 20, a cycloalkoxy group having a number of carbon atoms of 3 to 20, a fluoroalkoxy group having a number of carbon atoms of 1 to 20, an aryl group having a number of carbon atoms of 6 to 20 or an aryloxy group having a number of carbon atoms of 6 to 20, here, all of $R^{13}$ to $R^{17}$ do not simultaneously represent a hydrogen atom, and, when at least one of $R^{13}$ to $R^{17}$ is a fluoroalkyl group having a number of carbon atoms of 1 to 20, at least one of the remaining $R^{13}$ to $R^{17}$ is not a hydrogen atom or a fluoroalkyl group having a number of carbon atoms of 1 to 20, further, $R^{14}$ and $R^{15}$ may be linked to form a ring together with a carbon atom to which they are linked, and $R^{15}$ and $R^{16}$ may be linked to form a ring together with a carbon atom to which they are linked, and Z represents an anion.

15. The phosphonium salt according to claim 14, wherein $A^3$ and $A^4$ are a cyclopentyl group which may have an alkyl group having a number of carbon atoms of 1 to 20 or an aryl group having a number of carbon atoms of 6 to 20 as a substituent.

16. The phosphonium salt according to claim 14, wherein $A^3$ and $A^4$ are a cyclopentyl group.

17. The phosphonium salt according to claim 14, wherein at least one selected from $R^{13}$ and $R^{17}$ is an alkoxy group having a number of carbon atoms of 1 to 20.

18. The phosphonium salt according to claim 14, wherein $R^{14}$, $R^{15}$ and $R^{16}$ are a hydrogen atom.

19. A transition metal complex obtained by contacting the phosphine according to claim 9 and a group X transition metal compound.

* * * * *